US011430692B2

(12) United States Patent
Tsai et al.

(10) Patent No.: US 11,430,692 B2
(45) Date of Patent: Aug. 30, 2022

(54) THERMALLY STABLE COPPER-ALLOY ADHESION LAYER FOR METAL INTERCONNECT STRUCTURES AND METHODS FOR FORMING THE SAME

(71) Applicant: Taiwan Semiconductor Manufacturing Company Limited, Hsinchu (TW)

(72) Inventors: Cheng-Lun Tsai, Hsinchu (TW); Huei-Wen Hsieh, Hsinchu (TW); Chun-Sheng Chen, Hsinchu (TW); Kai-Shiang Kuo, Hsinchu (TW); Jen-Wei Liu, Hsinchu (TW); Cheng-Hui Weng, Hsinchu (TW); Chun-Chieh Lin, Taichung (TW); Hung-Wen Su, Hsinchu (TW)

(73) Assignee: Taiwan Semiconductor Manufacturing Company Limited, Hsinchu (TW)

( * ) Notice: Subject to any disclaimer, the term of this patent is extended or adjusted under 35 U.S.C. 154(b) by 19 days.

(21) Appl. No.: 16/941,751

(22) Filed: Jul. 29, 2020

(65) Prior Publication Data
US 2022/0037203 A1    Feb. 3, 2022

(51) Int. Cl.
*H01L 21/768* (2006.01)
*H01L 23/532* (2006.01)

(52) U.S. Cl.
CPC .. *H01L 21/76846* (2013.01); *H01L 21/76862* (2013.01); *H01L 21/76877* (2013.01); *H01L 23/53238* (2013.01)

(58) Field of Classification Search
CPC ......... H01L 23/53238; H01L 21/76843; H01L 21/76846; H01L 21/76849; H01L 21/76873
See application file for complete search history.

(56) References Cited

U.S. PATENT DOCUMENTS 6,037,258 A * 3/2000 Liu .................. H01L 21/7684
                                                  257/E21.583
6,395,642 B1 * 5/2002 Liu ...................... C25D 5/34
                                                  438/720
(Continued)

FOREIGN PATENT DOCUMENTS

TW          383478 B         3/2000

OTHER PUBLICATIONS

Taiwan Patent and Trademark Office, Application No. 110125283; Office Action dated Jul. 21, 2022, 8 pages.

*Primary Examiner* — Jaehwan Oh
*Assistant Examiner* — John M Parker
(74) *Attorney, Agent, or Firm* — The Marbury Law Group, PLLC

(57) ABSTRACT

An opening is formed through a dielectric material layer to physically expose a top surface of a conductive material portion in, or over, a substrate. A metallic nitride liner is formed on a sidewall of the opening and on the top surface of the conductive material portion. A metallic adhesion layer including an alloy of copper and at least one transition metal that is not copper is formed on an inner sidewall of the metallic nitride liner. A copper fill material portion may be formed on an inner sidewall of the metallic adhesion layer. The metallic adhesion layer is thermally stable, and remains free of holes during subsequent thermal processes, which may include reflow of the copper fill material portion. An additional copper fill material portion may be optionally deposited after a reflow process.

20 Claims, 30 Drawing Sheets

(56) References Cited

U.S. PATENT DOCUMENTS

| | | | |
|---|---|---|---|
| 6,432,819 B1* | 8/2002 | Pavate | H01L 23/53233 |
| | | | 438/676 |
| 7,070,687 B2* | 7/2006 | Chikarmane | C23C 18/1632 |
| | | | 205/123 |
| 8,623,762 B2* | 1/2014 | Kraft | H01L 23/3171 |
| | | | 438/667 |
| 2006/0199372 A1* | 9/2006 | Chung | H01L 21/28556 |
| | | | 438/628 |
| 2006/0290002 A1* | 12/2006 | Arana | H01L 21/76898 |
| | | | 257/774 |
| 2007/0080429 A1* | 4/2007 | Yang | H01L 21/76846 |
| | | | 257/632 |
| 2008/0206986 A1* | 8/2008 | Preusse | H01L 21/76846 |
| | | | 438/653 |
| 2011/0017499 A1* | 1/2011 | Yang | H01L 21/76846 |
| | | | 174/257 |
| 2016/0174375 A1* | 6/2016 | Mizushima | H01L 24/81 |
| | | | 174/262 |
| 2018/0025969 A1 | 1/2018 | Adusumilli et al. | |
| 2020/0176308 A1* | 6/2020 | Shen | H01L 21/76843 |
| 2020/0235055 A1* | 7/2020 | Hegde | H01L 23/53238 |
| 2020/0350201 A1* | 11/2020 | Motoyama | H01L 21/76847 |

* cited by examiner

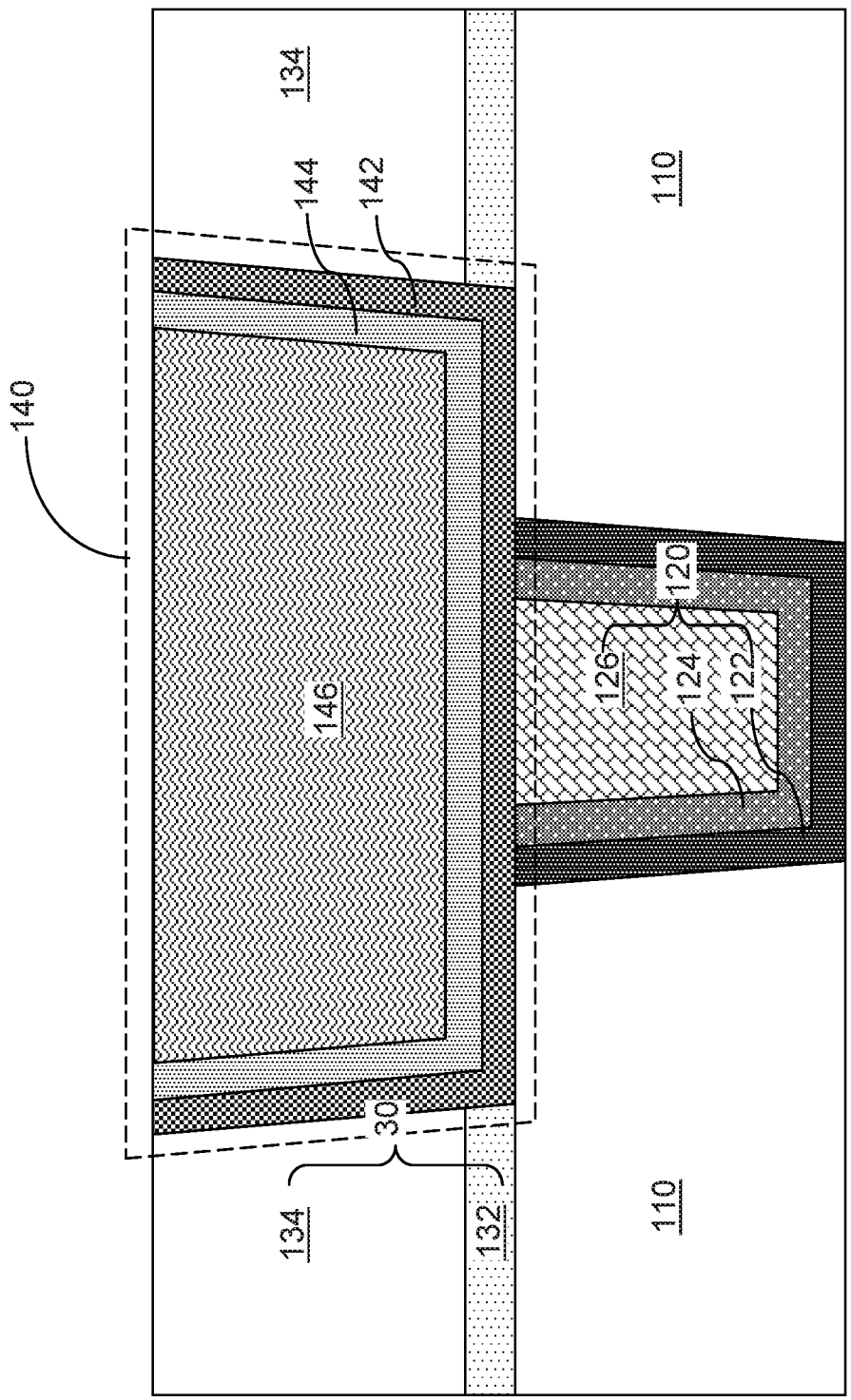

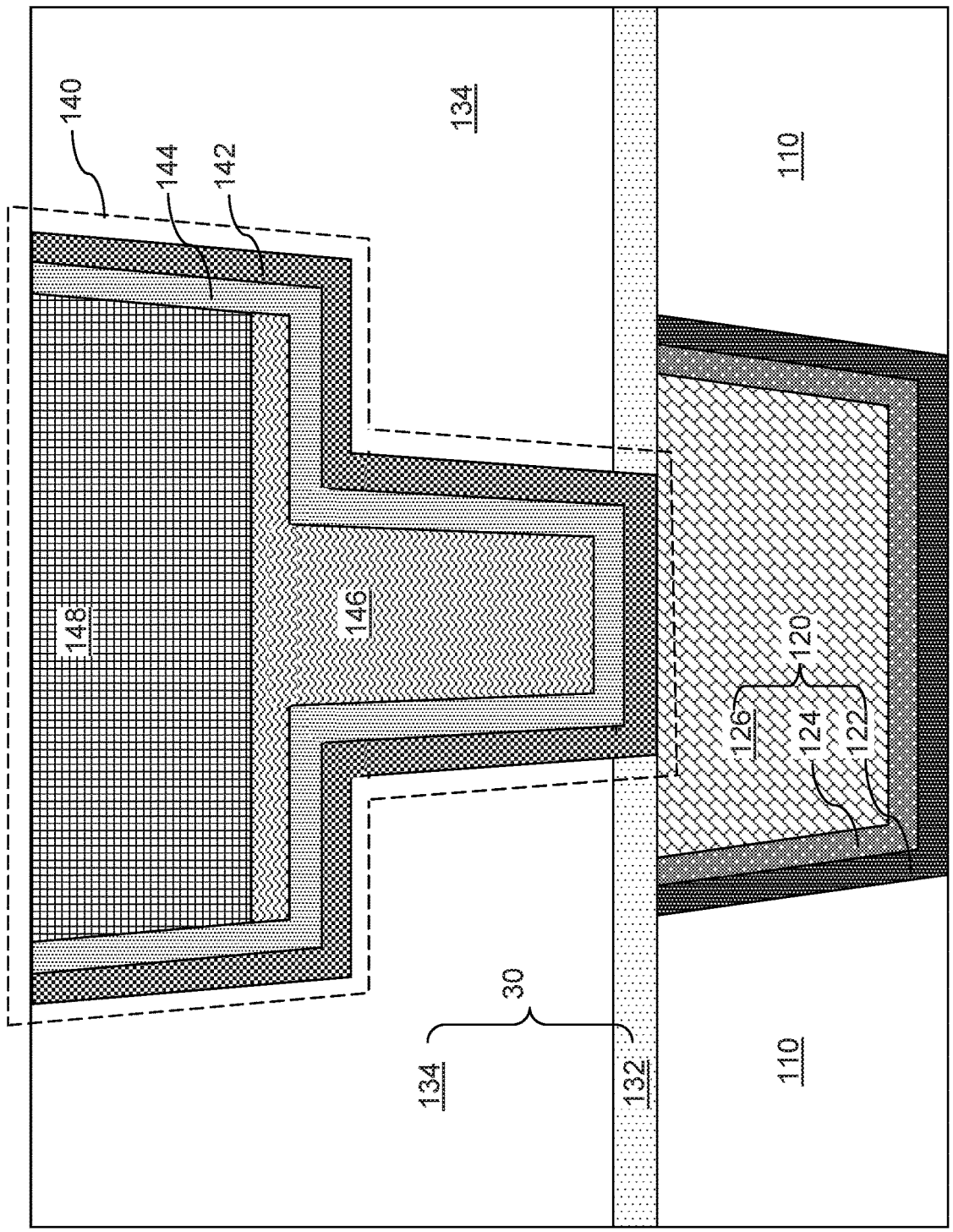

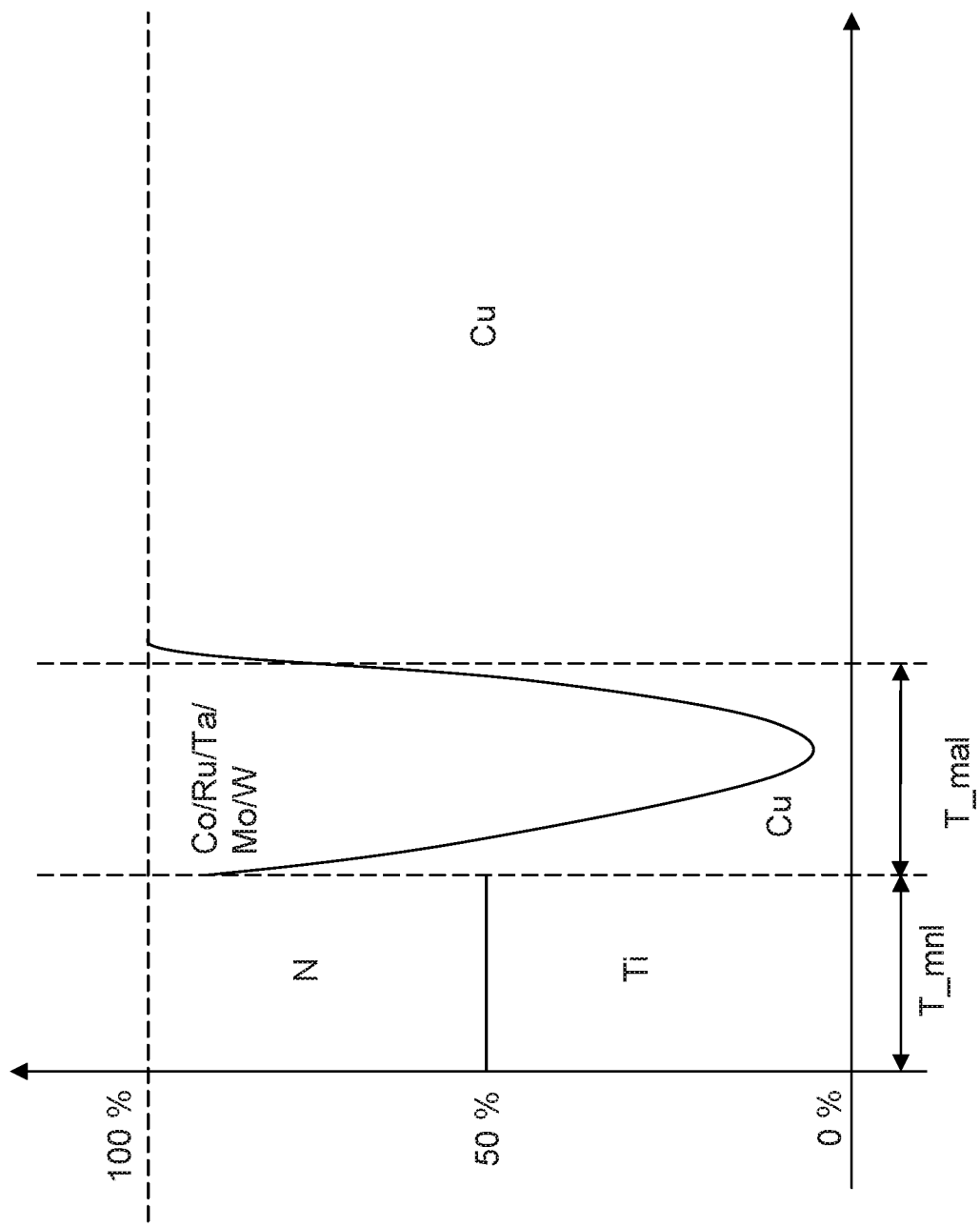

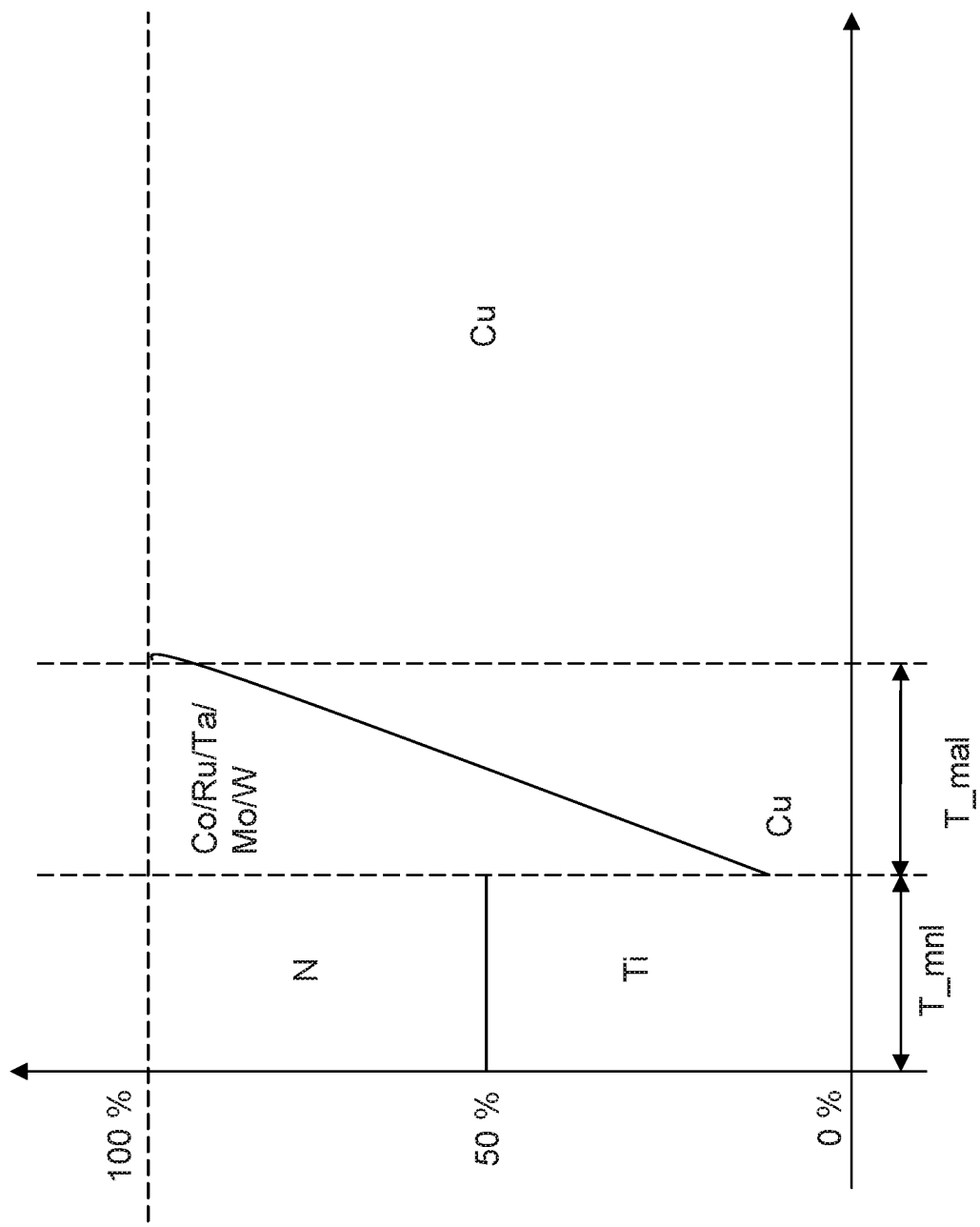

THERMALLY STABLE COPPER-ALLOY ADHESION LAYER FOR METAL INTERCONNECT STRUCTURES AND METHODS FOR FORMING THE SAME

BACKGROUND

Copper fill in narrow spaces is challenging because deposited copper does not typically provide full coverage of an underlying surfaces. As a result, voids may occur after deposition of copper. In particular, when copper is deposited to form fine-pitch copper interconnect structures, copper tends to agglomerate on an adhesion layer due to low mobility of copper on the adhesion layer. Further, insufficient thermal stability of the adhesion layer may form holes within the adhesion layer during a subsequent copper reflow process. Thus, copper fill in a fine-pitch copper interconnect structure is prone to generation of voids and causes electrical opens within the copper interconnect structure. Such defects adversely impact chip yield in advanced semiconductor devices.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 13A is a vertical cross-sectional view of a portion of a third alternative embodiment of the exemplary structure after formation of a metal interconnect structure according to an embodiment of the present disclosure.

FIG. 14A is a vertical cross-sectional view of a portion of a fourth alternative embodiment of the exemplary structure after formation of a metal interconnect structure according to an embodiment of the present disclosure.

FIGS. 16A-16D are diagrams illustrating material composition within the first, second, third, and fourth configurations of the metal interconnect structure of the exemplary structure of FIGS. 5A, 5B, 5C, and 5D, respectively.

DETAILED DESCRIPTION

Figure 1:
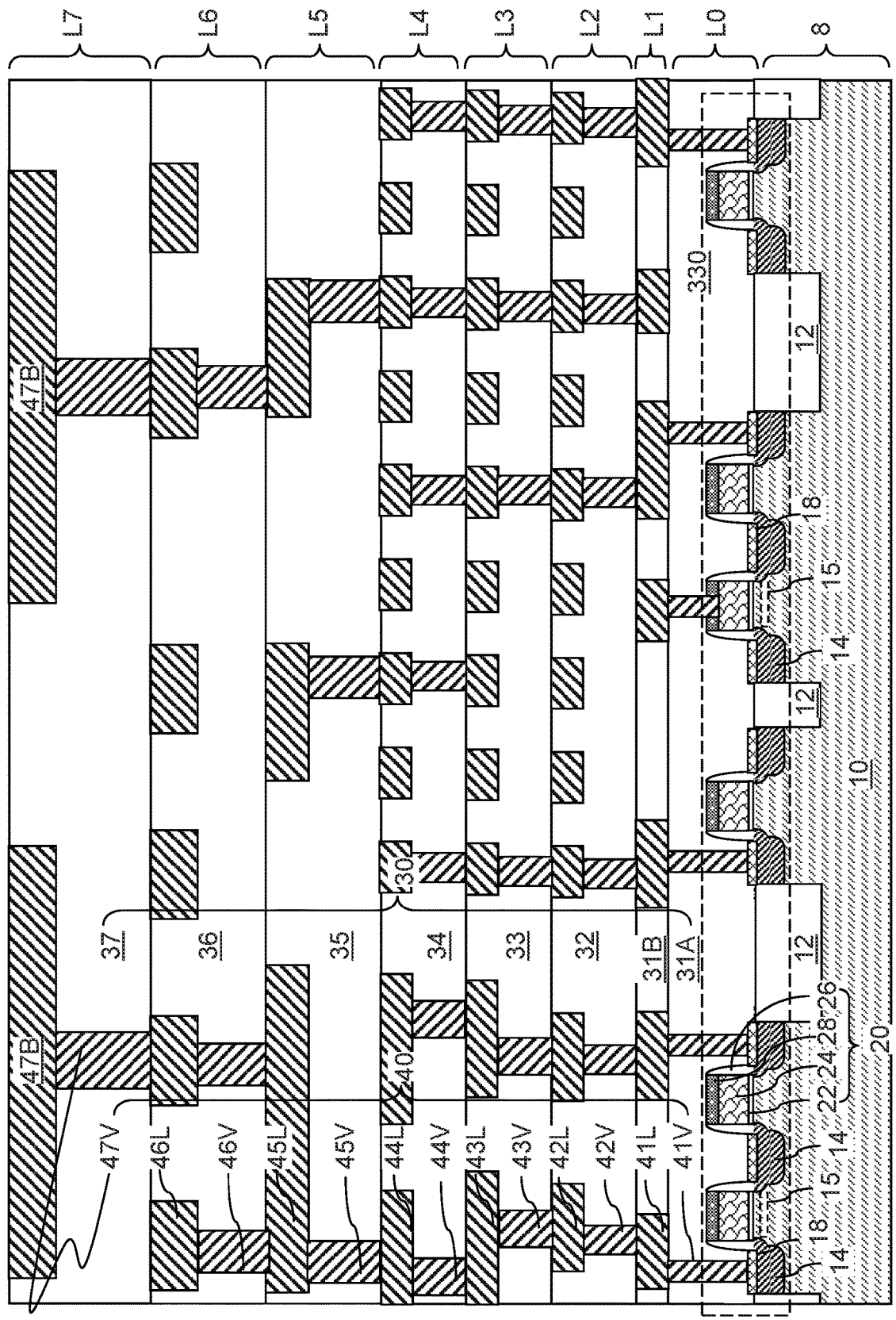
FIG. 1 is a vertical cross-sectional view of an exemplary structure including semiconductor devices and metal interconnect structures according to an embodiment of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly. Elements have the same reference numeral are presumed to have the same material composition unless expressly described otherwise.

The present disclosure is directed to semiconductor devices, and specifically to metal interconnect structures including thermally stable copper-alloy adhesion layer and methods of forming the same.

Generally, the structures and methods of the present disclosure may be used to form metal interconnect structures such as metal via structures, metal line structures, and integrated line and via structures that may be integrated into a semiconductor die including at least one semiconductor device. The metal interconnect structures of the present disclosure include a metallic nitride liner, a metallic adhesion layer including an alloy of copper and at least one non-copper transition metal, and a copper fill material portion that consists essentially of copper. The non-copper transition metal enhances adhesion between the copper fill material portion and the metallic nitride liner. Intermixing of copper with the at least one non-copper transition metal within the metallic adhesion layer increases thermal stability of the metallic adhesion layer so that the metallic adhesion layer remains conformal and does not form holes therethrough during subsequent anneal processes such as a reflow process for reflowing a copper material portion. The metallic adhesion layer may be formed by alternately forming at least one transition metal layer and at least one copper layer, and optionally inducing interdiffusion between the deposition material layers, or may be formed by simultaneous deposition of the at least one transition metal and copper. The enhanced adhesion provided by the metallic adhesion layer may provide metal interconnect structures including copper fill without voids, and may increase the yield of metal interconnect structures in semiconductor dies. The methods and structures of the present disclosure provide a continuous copper coverage on an adhesion layer, and thus, agglomeration of copper can be suppressed and a continuous copper fill structure without voids can be formed even at small dimensions. Various features of the structures and methods of the present disclosure are described in detail hereinbelow.

Referring to FIG. 1, an exemplary structure according to an embodiment of the present disclosure is illustrated, which includes semiconductor devices and metal interconnect structures. The exemplary structure includes a substrate 8 that contains a semiconductor material layer 10. The substrate 8 may include a bulk semiconductor substrate such as a silicon substrate in which the semiconductor material layer continuously extends from a top surface of the substrate 8 to a bottom surface of the substrate 8, or a semiconductor-on-insulator layer including the semiconductor material layer 10 as a top semiconductor layer overlying a buried insulator layer (such as a silicon oxide layer). The exemplary structure may include any semiconductor device known in the art, which may include field effect transistors, an array of memory cells, capacitors, inductors, antennas, and/or other passive devices.

For example, field effect transistors may be formed on, and/or in, the semiconductor material layer 10. In such an embodiment, shallow trench isolation structures 12 may be formed in an upper portion of the semiconductor material layer 10 by forming shallow trenches and subsequently filling the shallow trenches with a dielectric material such as silicon oxide. Various doped wells (not expressly shown) may be formed in various regions of the upper portion of the semiconductor material layer 10 by performing masked ion implantation processes.

Gate structures 20 may be formed over the top surface of the substrate 8 by depositing and patterning a gate dielectric layer, a gate electrode layer, and a gate cap dielectric layer. Each gate structure 20 may include a vertical stack of a gate dielectric 22, a gate electrode 24, and a dielectric gate cap 28. The vertical stack is herein referred to as a gate stack (22, 24, 28). Ion implantation processes may be performed to form extension implant regions, which may include source extension regions and drain extension regions. Dielectric gate spacers 26 may be formed around the gate stacks (22, 24, 28). Each assembly of a gate stack (22, 24, 28) and a dielectric gate spacer 26 constitutes a gate structure 20. Additional ion implantation processes may be performed using the gate structures 20 as self-aligned implantation masks to form deep active regions, which may include deep source regions and deep drain regions. Upper portions of the deep active regions may overlap with portions of the extension implantation regions. Each combination of an extension implantation region and a deep active region constitutes an active region 14, which may be a source region or a drain region depending on electrical biasing. A semiconductor channel 15 may be formed underneath each gate stack (22, 24, 28) between a neighboring pair of active regions 14. Metal-semiconductor alloy regions 18 may be formed on the top surface of each active region 14. Field effect transistors may be formed on the semiconductor material layer 10. Each field effect transistor may include a gate structure 20, a semiconductor channel 15, a pair of active regions 14 (one of which functions as a source region and another of which functions as a drain region), and optional metal-semiconductor alloy regions 18. A complementary metal-oxide-semiconductor (CMOS) circuit 330 may be provided on the semiconductor material layer 10, which may include a periphery circuit for the array(s) of resistive memory elements to be subsequently formed.

Various interconnect-level structures (L0, L1, L2, L3, L4, L5, L6, L7) may be subsequently formed. In an illustrative example, the interconnect-level structures (L0, L1, L2, L3, L4, L5, L6, L7) may include a contact-level structure L0, a first interconnect-level structure L1, and a second interconnect-level structure L2, a third interconnect-level structure L3, a fourth interconnect-level structure L4, a fifth interconnect-level structure L5, a sixth interconnect-level structure L6, and a seventh interconnect-level structure L7. While the present disclosure is described using an embodiment in which eight levels of interconnect-level structures (L0, L1, L2, L3, L4, L5, L6, L7) are used, embodiments are expressly contemplated herein in which the total number of levels in the interconnect-level structures (L0, L1, L2, L3, L4, L5, L6, L7) is 1 or any integer greater than 1.

The contact-level structure L0 may include a planarization dielectric layer 31A including a planarizable dielectric material such as silicon oxide and various contact via structures 41V contacting a respective one of the active regions 14 or the gate electrodes 24 and embedded within the planarization dielectric layer 31A. The first interconnect-level structure L1 includes a first interconnect-level dielectric layer 31B and first metal lines 41L embedded within the first interconnect-level dielectric layer 31B. The first interconnect-level dielectric layer 31B is also referred to as a first line-level dielectric layer. The first metal lines 41L may contact a respective one of the contact via structures 41V. The second interconnect-level structure L2 includes a second interconnect-level dielectric layer 32, which may include a stack of a first via-level dielectric material layer and a second line-level dielectric material layer, or a line-and-via-level dielectric material layer. The second interconnect-level dielectric layer 32 embeds second interconnect-level metal interconnect structures (42V, 42L), which includes first metal via structures 42V and second metal lines 42L. Top surfaces of the second metal lines 42L may be coplanar with the top surface of the second interconnect-level dielectric layer 32.

The third interconnect-level structure L3 may include a fourth interconnect-level dielectric layer 33 embedding fourth interconnect-level metal interconnect structures (43V, 43L), which may include third metal via structures 43V and fourth metal lines 43L. The third interconnect-level metal interconnect structures (43V, 43L) may include second metal via structures 43V and third metal lines 43L. The fourth interconnect-level structure L4 may include a fourth interconnect-level dielectric layer 34 embedding fourth interconnect-level metal interconnect structures (44V, 44L), which may include third metal via structures 44V and fourth metal lines 44L. The fifth interconnect-level structure L5 may include a fifth interconnect-level dielectric layer 35 embedding fifth interconnect-level metal interconnect structures (45V, 45L), which may include fourth metal via structures 45V and fifth metal lines 45L. The sixth interconnect-level structure L6 may include a sixth interconnect-level dielectric layer 36 embedding sixth interconnect-level metal interconnect structures (46V, 46L), which may include fifth metal via structures 46V and sixth metal lines 46L. The seventh interconnect-level structure L7 may include a seventh interconnect-level dielectric layer 37 embedding sixth metal via structures 47V (which are seventh interconnect-level metal interconnect structures) and metal bonding pads 47B. The metal bonding pads 47B may be configured for solder bonding (which may use C4 ball bonding or wire bonding), or may be configured for metal-to-metal bonding (such as copper-to-copper bonding).

Each interconnect-level dielectric layer may be referred to as an interconnect-level dielectric (ILD) layer 30. Each interconnect-level metal interconnect structures may be referred to as a metal interconnect structure 40. Each combination of a metal via structure and an overlying metal line located within a same interconnect-level structure (L2-L7) may be formed sequentially as two distinct structures by using two single damascene processes, or may be simultaneously formed as a unitary structure using a dual damascene process. Each of the metal interconnect structure 40 may include a respective metallic liner (such as a layer of TiN, TaN, or WN having a thickness in a range from 2 nm to 20 nm) and a respective metallic fill material (such as W, Cu, Co, Mo, Ru, other elemental metals, or an alloy or a combination thereof). Various etch stop dielectric layers (not expressly shown) and dielectric capping layers (not expressly shown) may be inserted between vertically neighboring pairs of ILD layers 30, or may be incorporated into one or more of the ILD layers 30.

Figure 2:
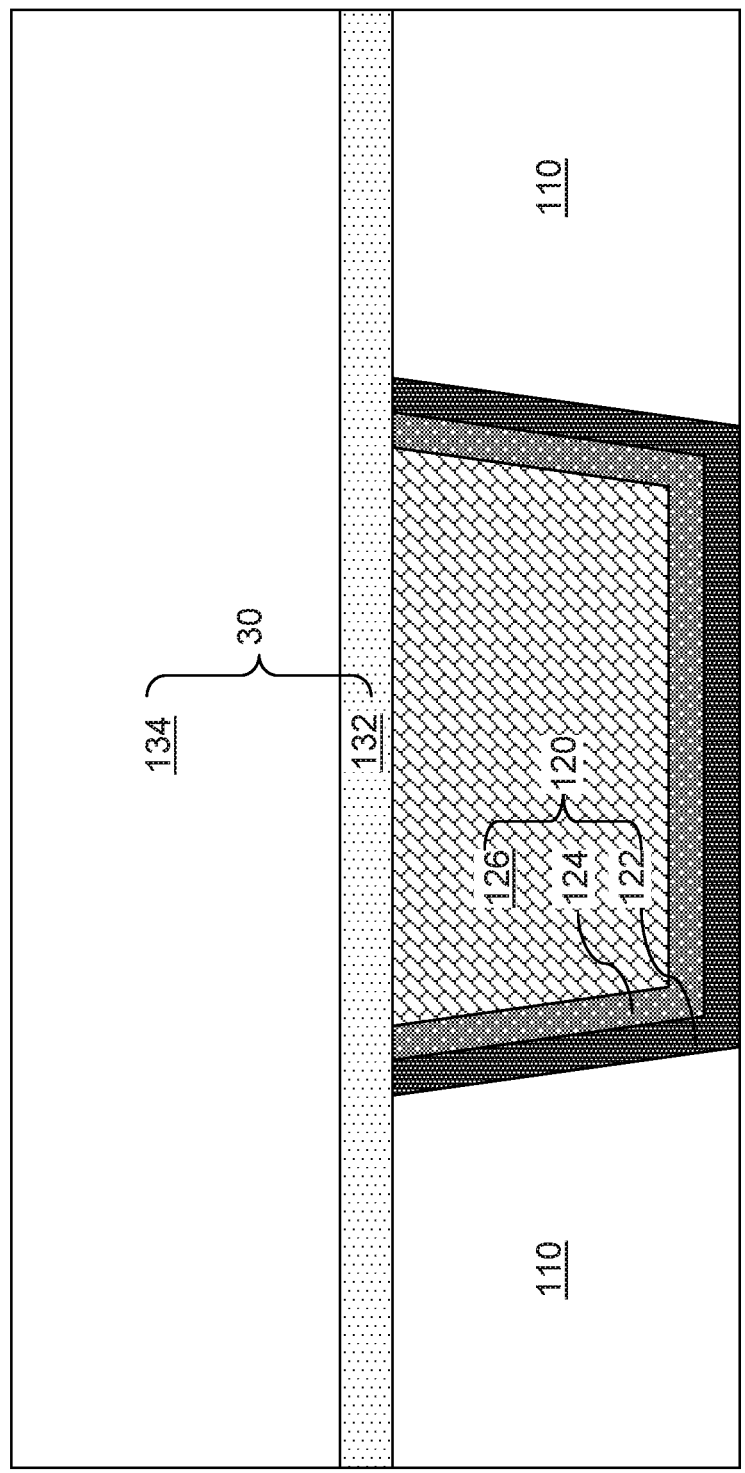
FIG. 2 is vertical cross-sectional view of a portion of the exemplary structure after formation of an underlying conductive material portion, an etch stop dielectric layer, and a dielectric material layer according to an embodiment of the present disclosure.

Referring to FIG. 2, a portion of the exemplary structure of FIG. 1 is illustrated during manufacture. The illustrated portion of FIG. 2 includes a interconnect-level dielectric layer 30, which may be any one of the dielectric material layers (e.g., 31-37) illustrated in FIG. 1. The illustrated interconnect-level dielectric layer 30 includes a dielectric material layer 134 that includes an interconnect-level dielectric (ILD) material such as undoped silicate glass, a doped silicate glass, non-porous organosilicate glass (a SiCOH dielectric), or a porous organosilicate glass. In one embodiment, the dielectric material layer 134 may include, and/or may consist essentially of, a porous dielectric material having a dielectric constant (k) in a range from 1.4 to 2.7. The thickness of the dielectric material layer 134 may be in a range from 50 nm to 600 nm, such as from 100 nm to 300 nm, although lesser and greater thicknesses may also be used. Optionally, the interconnect-level dielectric layer 30 may include an etch stop dielectric layer 132, which may be formed prior to formation of the dielectric material layer 134. The etch stop dielectric layer 132 may include a dielectric material providing higher etch resistance than the dielectric material layer 134 during an anisotropic etch process. For example, the etch stop dielectric layer 132 may include silicon carbide nitride, silicon oxynitride, or silicon nitride. The thickness of the etch stop dielectric layer 132 may be in a range from 3 nm to 30 nm, although lesser and greater thicknesses may also be used.

An underlying conductive material portion 120 is also illustrated, which underlies the interconnect-level dielectric layer 30. The underlying conductive material portion 120 may be embedded in an underlying matrix layer 110. In one embodiment, the underlying conductive material portion 120 may be any one of the metal interconnect structures 40 other than the topmost metal interconnect structures, i.e., any metal interconnect structure 40 other than the metal bonding pads 47B. In one embodiment, the underlying conductive material portion 120 may be a metal via structure, a metal line structure, or an integrated line and via structure. In such an embodiment, the underlying matrix layer 110 may be another interconnect-level dielectric layer 30 that underlies the overlying interconnect-level dielectric layer 30. Alternatively, the underlying conductive material portion 120 may be a conductive component (i.e., a node) of a semiconductor device such as a metal-semiconductor alloy region 18 or an active region 14 (such as a source region or a drain region) of a field effect transistor, or a gate electrode 24 of a field effect transistor. In such an embodiment, the underlying matrix layer 110 may be the matrix material layer that laterally surrounds the conductive component such as a semiconductor material layer 10 and/or a shallow trench isolation structure 12, or a dielectric gate spacer 26 and/or a bottommost one of the interconnect-level dielectric layers 30 that laterally surrounds the gate electrode 24. Generally, a semiconductor device may be formed on the substrate 8, and the conductive material portion 120 may comprise a node of the semiconductor device or an additional metal interconnect structure 40 overlying the substrate 8 and electrically connected to the node of the semiconductor device.

In an illustrative example, in embodiments in which the underlying metal interconnect structure 120 comprises a metal via structure, a metal line structure, or an integrated line and via structure, the underlying metal interconnect structure 120 may include a metallic nitride liner 122, an optional metallic adhesion layer 124, and a metal fill material portion 126. In some embodiments, the metallic nitride liner 122 may have the same material composition as the metallic nitride liner of a metal interconnect structure to be subsequently formed within the interconnect-level dielectric layer 30, and the metal fill material portion 126 may be a copper fill material portion consisting essentially of copper. Alternatively, the metal fill material portion 126 of the underlying metal interconnect structure 120 may include a metal other than copper, which may include tungsten, molybdenum, cobalt, ruthenium, etc. Other suitable metal fill materials are within the contemplated scope of disclosure.

Figure 3:
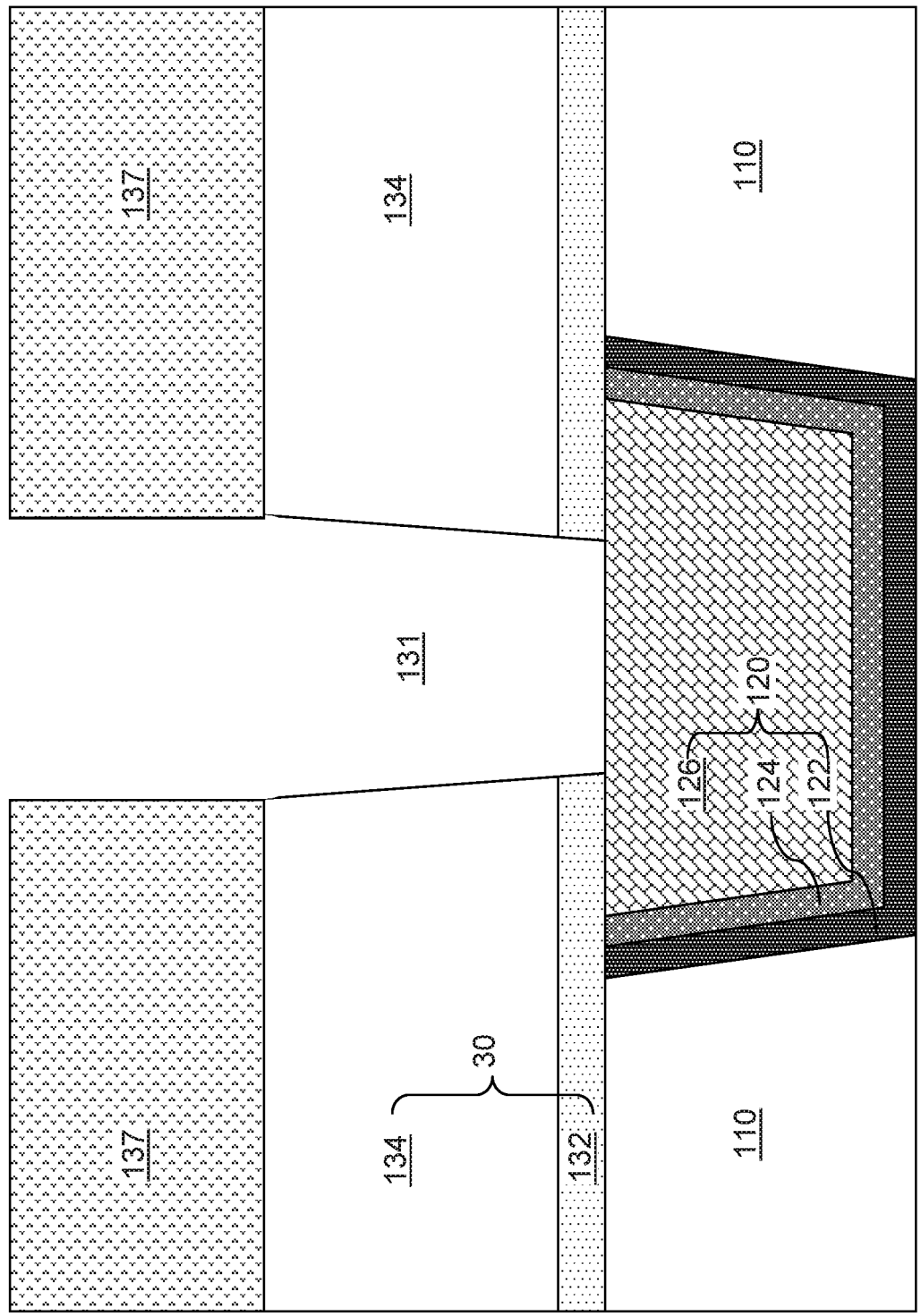
FIG. 3 is a vertical cross-sectional view of the portion of the exemplary structure after formation of an opening through the dielectric material layer according to an embodiment of the present disclosure.

Referring to FIG. 3, a photoresist layer 137 may be applied over the top surface of the interconnect-level dielectric layer 30. The photoresist layer 137 may be lithographically patterned to form openings therethrough. While the illustrated region in FIG. 3 includes only one opening, one of ordinary skill in the art would understand that multiple openings may be formed through the photoresist layer 137. The multiple openings may include a pattern of metal line structures, or may include a pattern of metal via structures. The pattern in the photoresist layer 137 may be transferred through the interconnect-level dielectric layer 30 by performing an anisotropic etch process. Openings 131 may be formed through the interconnect-level dielectric layer 30. The openings 131 vertically extend from a top surface of the interconnect-level dielectric layer 30 to a bottom surface of the interconnect-level dielectric layer 30. A top surface of the underlying metal interconnect structure 120 may be physically exposed at the bottom of each opening 131 through the interconnect-level dielectric layer 30. The photoresist layer 137 may be subsequently removed, for example, by ashing. Alternatively, two lithographic patterning processes using two photoresist layers 137 and two anisotropic etch processes may be performed in lieu of a combination of a single lithographic patterning process and a single anisotropic etch process to form integrated line and via cavities as the openings 131. An integrated line and via cavity includes at least one via-shaped opening at a lower portion and a line cavity that is connected to each of the at least one via-shaped opening at an upper portion.

The aspect ratio of each opening 131 (i.e., the ratio of the depth of the opening 131 to the width of the opening 131) may be in a range from 0.01 to 30, although lesser and greater aspect ratios may also be used. In some embodiment, an opening 131 may have an aspect ratio in a range from 1 to 30, such as from 3 to 15. In such embodiments, filling the entire volume of the opening 131 may be a challenge, and the methods and structures of the present disclosure may provide significant advantage in forming a completely filled metal interconnect structure. However, it should be understood that the benefits of the methods and structures of the present disclosure may be obtained even when the aspect ratio of an opening is less than 3, such as less than 1.

While the illustrated portion of the exemplary structure shows a stand-alone opening 131, it is understood that the openings 131 through the interconnect-level dielectric layer 30 may be formed in an array configuration. For example, if the interconnect-level dielectric layer 30 includes a line-level dielectric material layer, the openings 131 may be formed as a one-dimensional periodic array of line cavities that laterally extend along a same horizontal direction. In some embodiments, the pitch of the one-dimensional periodic array of line cavities may be a lithographic minimum pitch, i.e., a minimum pitch that may be printed using the lithographic exposure and development tool that is used to form the openings 131. If the interconnect-level dielectric layer 30 includes a via-level interconnect-level dielectric layer, the openings 131 may be formed as an array of via cavities, which may include a two-dimensional array of via cavities or a one-dimensional array of via cavities. In some embodiments, the pitch of via cavities may be a lithographic minimum pitch. In some embodiments, the openings 131 may be formed with a periodic pitch along at least one horizontal direction, and the periodic pitch may be in a range from 10 nm to 200 nm, such as from 20 nm to 100 nm.

The horizontal directions and the vertical directions of the drawings of the instant application may have different scales. The methods and structures of the present disclosure may be used for a wide range of aspect ratios. For example, the aspect ratio of an opening in which a metal interconnect structure of the present disclosure may be formed may be greater than 1, and may be in a range from 1 to 30, such as from 2 to 15. Further, while FIG. 3 illustrates an embodiment in which an opening 131 though the interconnect-level dielectric layer 30 has a lesser width than the underlying metal interconnect structure 120, embodiments are expressly contemplated in which the opening 131 has a greater width than the underlying metal interconnect structure 120.

Figure 4:
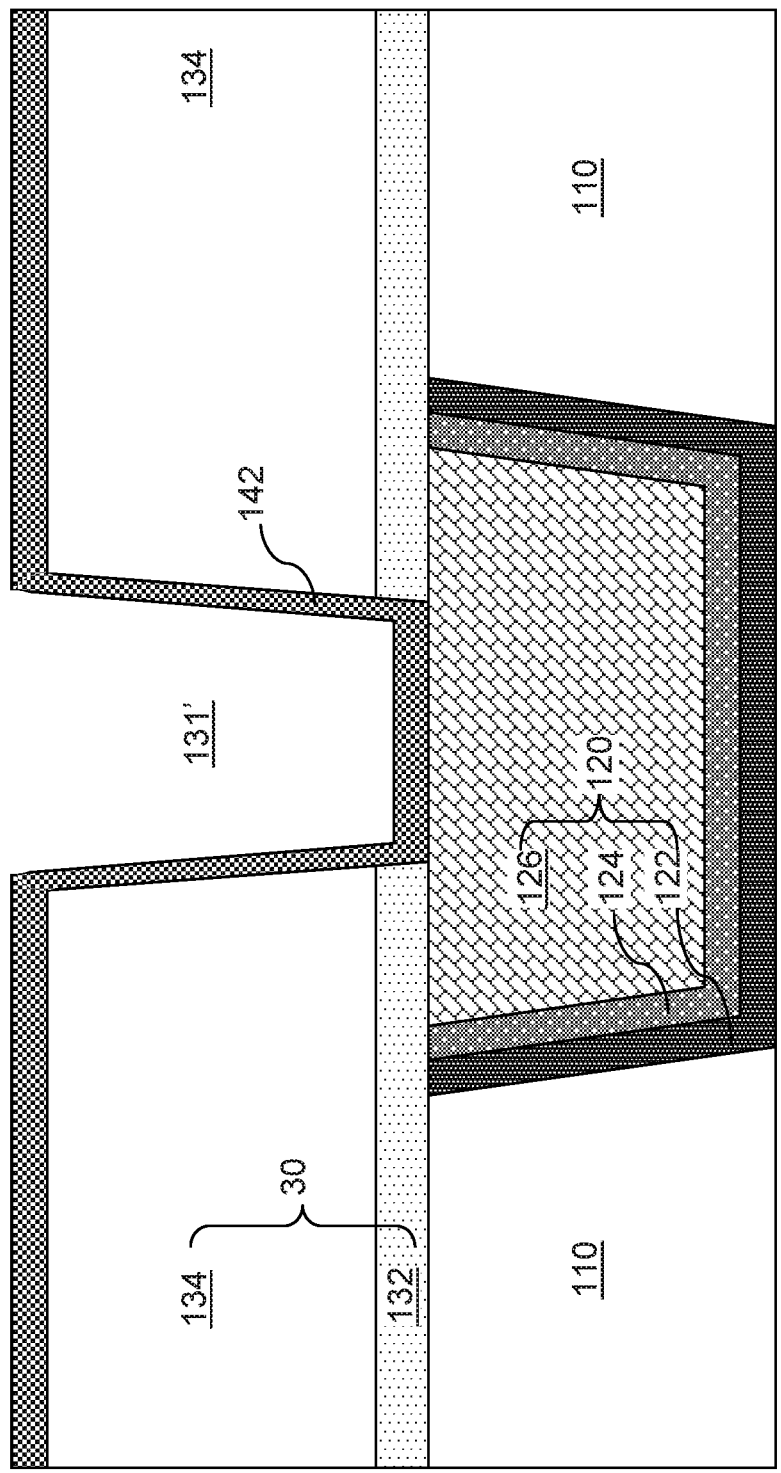
FIG. 4 is a vertical cross-sectional view of the portion of the exemplary structure after formation of a metallic nitride liner according to an embodiment of the present disclosure.

Referring to FIG. 4, a metallic nitride liner 142 may be optionally formed in each opening 131 through the interconnect-level dielectric layer 30 and over the top surface of the interconnect-level dielectric layer 30. The metallic nitride liner 142 is an optional component, and as such, may, or may not, be formed. The metallic nitride liner 142 includes a conductive metallic material such as TiN, TaN, WN, an alloy thereof, or a stack thereof. The metallic nitride liner 142 may be formed by physical vapor deposition, chemical vapor deposition, or atomic layer deposition. The thickness of the metallic nitride liner 142 as measured on a sidewall of each opening 131 through the interconnect-level dielectric layer 30 may be in a range from 0.5 nm to 5 nm, such as from 1 nm to 3 nm, although lesser and greater thicknesses may also be used. The metallic nitride liner 142 may contact the physically exposed top surface of the underlying metal interconnect structure 120, the sidewall of each opening through the interconnect-level dielectric layer 30, and over the top surface of the interconnect-level dielectric layer 30. A cavity 131' is present in an unfilled volume of each opening 131.

FIGS. 5A-5D illustrate various configurations of the exemplary structure during a subsequent processing step, in which a metallic adhesion layer 144 may be formed on the metallic nitride liner 142. Generally, the metallic adhesion layer 144 comprises, and/or consists essentially of, an alloy of copper and at least one transition metal that is not copper.

The at least one transition metal may be a single transition metal, or a plurality of transition metals. The at least one transition metal may include one or more transition metal that may enhance adhesion of copper to the material of metallic nitride liner 142 in an alloy form with copper. For example, the at least one transition metal may include one or more elements selected from Co, Ru, Ta, Mo, and W. The metallic adhesion layer 144 may be deposited directly on inner sidewalls of the metallic nitride liner 142 and directly on horizontal surfaces of the metallic nitride liner 142.

Figure 5A:
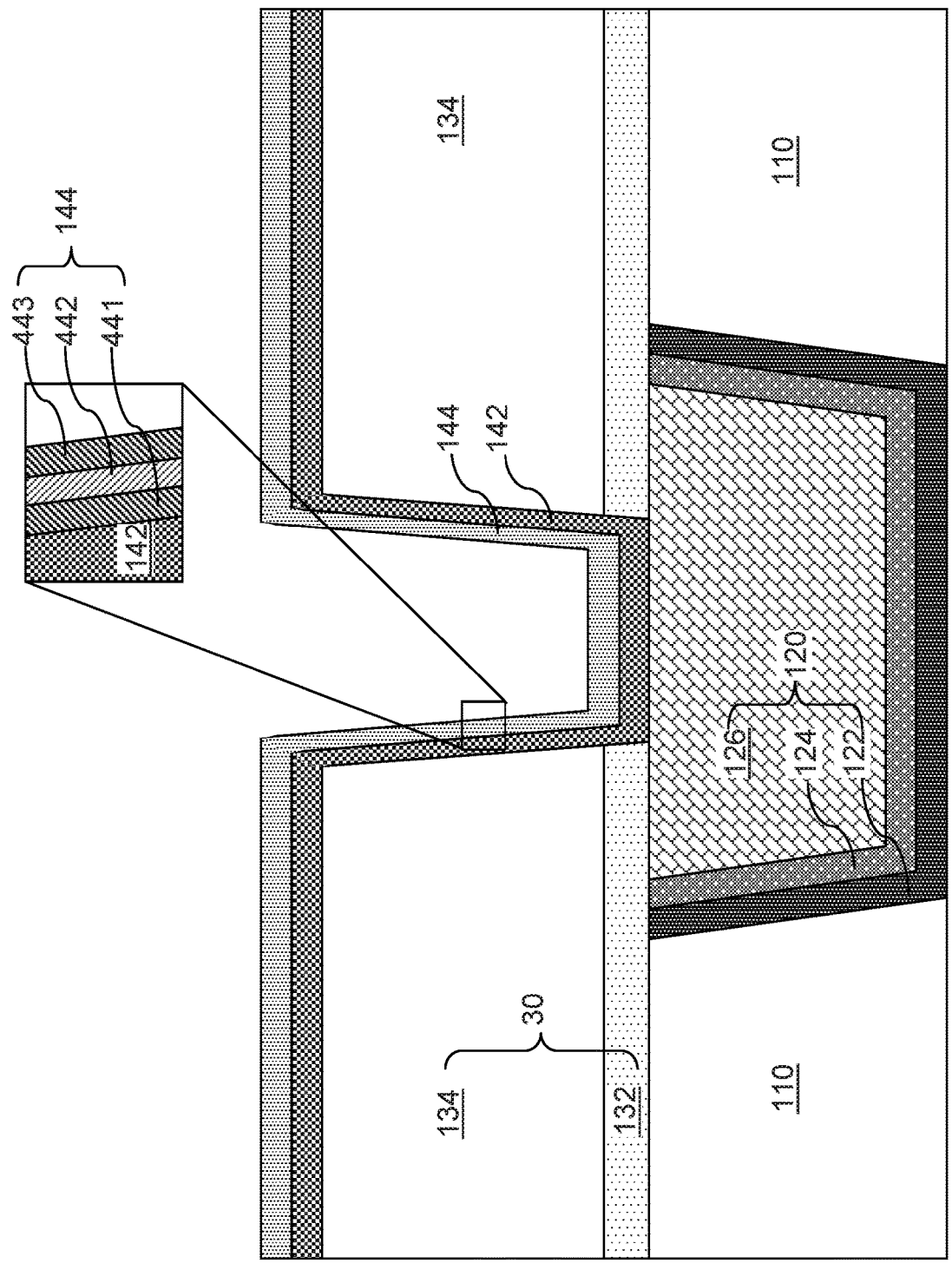
FIG. 5A is a vertical cross-sectional view of the portion of the exemplary structure after formation of a metallic adhesion layer having a first configuration according to an embodiment of the present disclosure.

Referring to FIG. 5A, a first configuration of the exemplary structure is illustrated, which includes a metallic adhesion layer 144 formed by deposition of a stack of at least one transition metal layer (441, 443) and at least one copper layer 442. Each of the at least one transition metal layer (441, 443) may consist essentially of at least one transition metal such as at least one elemental metal selected from Co, Ru, Ta, Mo, and W. In one embodiment, each of the at least one transition metal layer (441, 443) consists essentially of a single transition metal selected from Co, Ru, Ta, Mo, and W. In embodiments in which two or more transition metal layers (441, 443) are present, the two or more transition metal layers (441, 443) may consist essentially of a same transition metal, or may include multiple transition metal. In other words, different transition metal layers (441, 443) may include different transition metal elements. In another embodiment, one or more of the at least one transition metal layer (441, 443) may include, and/or may consist essentially of, an intermetallic alloy of at least two transition metal elements. For example, the intermetallic alloy may include, and/or may consist essentially of, an intermetallic alloy of Co, Ru, Ta, Mo, and/or W. In one embodiment, each of the at least one transition metal layer (441, 443) consists essentially of cobalt. Each of the at least one copper layer 442 may consists essentially of copper. The at least one copper layer 442 may include a single copper layer or a plurality of copper layers.

In one embodiment, one or more of the at least one copper layer 442 may be deposited prior to deposition of one of the at least one transition metal layer (441, 443). In other words, one or more of the at least one copper layer 442 may be deposited prior to deposition of the transition metal layer that most distal from the metallic nitride liner 142 (i.e., the last metallic nitride liner to be deposited). In one embodiment, the at least one transition metal layer (441, 443) comprises at least two transition metal layers (441, 443), and one of the at least one copper layer 442 may be deposited after deposition of one of the at least two transition metal layers (such as a first transition metal layer 441) and prior to deposition of another of the at least two transition metal layers (such as a second transition metal layer 443).

Each of the at least one transition metal layer (441, 443) may be formed by physical vapor deposition (sputtering), chemical vapor deposition, or atomic layer deposition. Each of the at least one copper layer 442 may be formed by physical vapor deposition (sputtering), chemical vapor deposition, or atomic layer deposition. The total thickness of the metallic adhesion layer 144, i.e., the sum of the thicknesses of all of the at least one transition metal layer (441, 443) and at least one copper layer 442, may be in a range from 0.5 nm to 10 nm, such as from 1 nm to 6 nm, although lesser and greater thicknesses may also be used. The thickness of each of the at least one transition metal layer (441, 443) may be about 1 monolayer, less than 1 monolayer, or more than 1 monolayer. The thickness of each of the at least one copper layer 442 may be about 1 monolayer, less than 1 monolayer, or more than 1 monolayer.

The atoms of the at least one transition metal layer (441, 443) and the at least one copper layer 442 interdiffuse in embodiments in which one or more of the at least one transition metal layer (441, 443) and the at least one copper layer 442 have a thickness of less than 1 monolayer. Additionally or alternatively, the atoms of the at least one transition metal layer (441, 443) and the at least one copper layer 442 thermally interdiffuse during deposition of the at least one transition metal layer (441, 443) and the at least one copper layer 442 and/or during a subsequent thermal processing step. In embodiments in which the interdiffusion of the transition metal atoms and copper atoms from the at least one transition metal layer (441, 443) and the at least one copper layer 442 is not complete, the metallic adhesion layer 144 may have a compositional modulation as a function of a distance from the metallic nitride liner 142. In other words, in embodiments in which the composition of the metallic nitride liner 142 is not completely homogenized through interdiffusion, the metallic adhesion layer 144 may have a compositional modulation as a function of a distance from the metallic nitride liner 142.

Optionally, interdiffusion among atoms of the at least one transition metal layer (441, 443) and the at least one copper layer 442 may be enhanced by performing a plasma treatment process or a thermal anneal process. In one embodiment, enhancing compositional uniformity of a layer stack including the at least one transition metal layer (441, 443) and the at least one copper layer 442 may be effectuated by performing a plasma treatment process on the layer stack. For example, a hydrogen plasma treatment process may be performed to increase the interdiffusion among atoms of the at least one transition metal layer (441, 443) and the at least one copper layer 442. In one embodiment, enhancing compositional uniformity of the layer stack including the at least one transition metal layer (441, 443) and the at least one copper layer 442 may be effectuated by performing a thermal anneal process. The elevated temperature of the thermal anneal may be in a range from 150 degrees Celsius to 400 degrees Celsius, such as from 200 degrees Celsius to 350 degrees Celsius.

Upon formation, and after the optional compositional homogenization process (if used), the metallic adhesion layer 144 may have a compositional modulation as a function of a distance from the metallic nitride liner 142, for example, as a function of a distance from an inner sidewall of the metallic nitride liner 142. In some embodiments, the position of a local peak atomic concentration of the at least one transition metal within the metallic adhesion layer 142 may be spaced from an outer sidewall of the metallic adhesion layer 144 (such as an interface between the metallic nitride liner 142 and the metallic adhesion layer 144). For example, the distance between the position of the local peak atomic concentration of the at least one transition metal and the outer sidewall of the metallic adhesion layer 144 (such as the interface between the metallic nitride liner 142 and the metallic adhesion layer 144) may be in a range from 10% to 100% of a thickness of the metallic adhesion layer 144 (such as the thickness of a vertical or tapered portion of the metallic adhesion layer 144 that contacts a sidewall of the interconnect-level dielectric layer 30). In some embodiments, the atomic concentration of copper within the metallic adhesion layer 144 may have a minimum at a location that is spaced from the outer sidewall of the metallic adhesion layer 144 (such as the interface between the metallic nitride liner 142 and the metallic adhesion layer 144). In some embodiments, the distance between the location of the minimum of the atomic concentration of copper within the metallic adhesion layer 144 and an outer sidewall of the metallic adhesion layer 144 (such as an interface between the metallic nitride liner 142 and the metallic adhesion layer 144) may be in a range from 10% to 100% of the thickness of the metallic adhesion layer 144 (such as the thickness of the metallic adhesion layer 144 over a sidewall of the interconnect-level dielectric layer 30).

While FIG. 5A illustrates a configuration in which the metallic adhesion layer 144 is formed by deposition of two transition metal layers (441, 443) and one copper layer 442, configurations are expressly contemplated herein in which two or more transition metal layers are interlaced with two or more copper layers. The total number of the transition metal layers (441, 443) may be generally in a range from 1 to 5, and the total number of copper layers 442 may be generally in a range from 1 to 5.

Figure 5B:
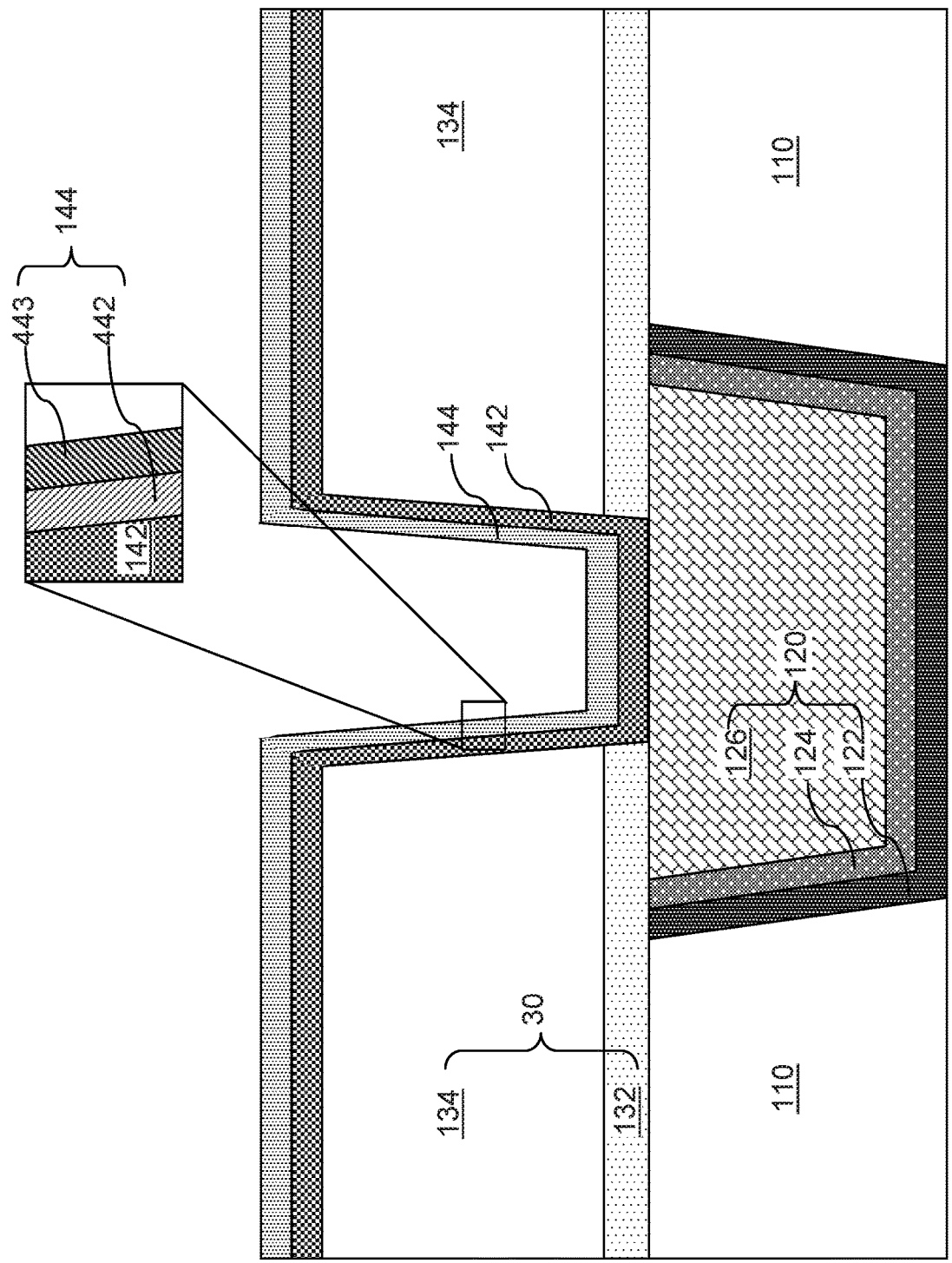
FIG. 5B is a vertical cross-sectional view of the portion of the exemplary structure after formation of a metallic adhesion layer having a second configuration according to an embodiment of the present disclosure.

Referring to FIG. 5B, a second configuration of the exemplary structure is illustrated, which includes a metallic adhesion layer 144 formed by deposition of a stack of a copper layer 442 and a transition metal layer 443. In this configuration, the copper layer 442 may be deposited first, and the transition metal layer 443 may be deposited on the copper layer 442. The copper layer 442 consists essentially of copper. The transition metal layer 443 may have the same material composition as any of the transition metal layers (441, 443) in the first configuration of the exemplary structure illustrated in FIG. 5A. For example, the transition metal layer 443 may consist essentially of at least one transition metal such as at least one elemental metal selected from Co, Ru, Ta, Mo, and W. In one embodiment, the transition metal layer 443 consists essentially of a single transition metal selected from Co, Ru, Ta, Mo, and W. In another embodiment, the transition metal layer 443 may consist essentially of, an intermetallic alloy of at least two transition metal elements. For example, the intermetallic alloy may include, and/or may consist essentially of, an intermetallic alloy of Co, Ru, Ta, Mo, and/or W. In one embodiment, the transition metal layer 443 consists essentially of cobalt.

The copper layer 442 may be formed by physical vapor deposition (sputtering), chemical vapor deposition, or atomic layer deposition. The transition metal layer 443 may be formed by physical vapor deposition (sputtering), chemical vapor deposition, or atomic layer deposition. The total thickness of the metallic adhesion layer 144, i.e., the sum of the thicknesses of the transition metal layer 443 and the copper layer 442, may be in a range from 0.5 nm to 10 nm, such as from 1 nm to 6 nm, although lesser and greater thicknesses may also be used. The thickness of the transition metal layer 443 may be about 1 monolayer, less than 1 monolayer, or more than 1 monolayer. The thickness of the copper layer 442 may be about 1 monolayer, less than 1 monolayer, or more than 1 monolayer.

The atoms of the transition metal layer 443 and the copper layer 442 interdiffuse in embodiments in which one or more of the transition metal layer 443 and the copper layer 442 have a thickness of less than 1 monolayer. Additionally or alternatively, the atoms of the transition metal layer 443 and the copper layer 442 thermally interdiffuse during deposition of the transition metal layer 443 and/or during a subsequent thermal processing step. In embodiments in which the interdiffusion of the transition metal atoms and copper atoms from the transition metal layer 443 and the copper layer 442 is not complete, the metallic adhesion layer 144 may have a compositional modulation as a function of a distance from the metallic nitride liner 142. In other words, in embodiments in which the composition of the metallic nitride liner 142 is not completely homogenized through interdiffusion, the metallic adhesion layer 144 may have a compositional modulation as a function of a distance from the metallic nitride liner 142.

Optionally, interdiffusion among atoms of the transition metal layer 443 and the copper layer 442 may be enhanced by performing a plasma treatment process or a thermal anneal process. In one embodiment, enhancing compositional uniformity of a layer stack including the transition metal layer 443 and the copper layer 442 may be effectuated by performing a plasma treatment process on the layer stack. For example, a hydrogen plasma treatment process may be performed to increase the interdiffusion among atoms of the transition metal layer 443 and the copper layer 442. In one embodiment, enhancing compositional uniformity of the layer stack including the transition metal layer 443 and the copper layer 442 may be effectuated by performing a thermal anneal process.

Upon formation, and after the optional compositional homogenization process (if used), the metallic adhesion layer 144 may have a compositional modulation as a function of a distance from the metallic nitride liner 142, for example, as a function of a distance from an inner sidewall of the metallic nitride liner 142. In some embodiments, the position of a local peak atomic concentration of the at least one transition metal within the metallic adhesion layer 142 may be spaced from an outer sidewall of the metallic adhesion layer 144 (such as an interface between the metallic nitride liner 142 and the metallic adhesion layer 144). In some embodiment, the local peak atomic concentration of the at least one transition metal within the metallic adhesion layer 142 may be located on a physically exposed inner sidewall of the metallic adhesion layer 142. In some embodiments, the atomic concentration of copper within the metallic adhesion layer 144 may have a local maximum at an outer sidewall of the metallic adhesion layer 144 (such as an interface between the metallic nitride liner 142 and the metallic adhesion layer 144).

Figure 5C:
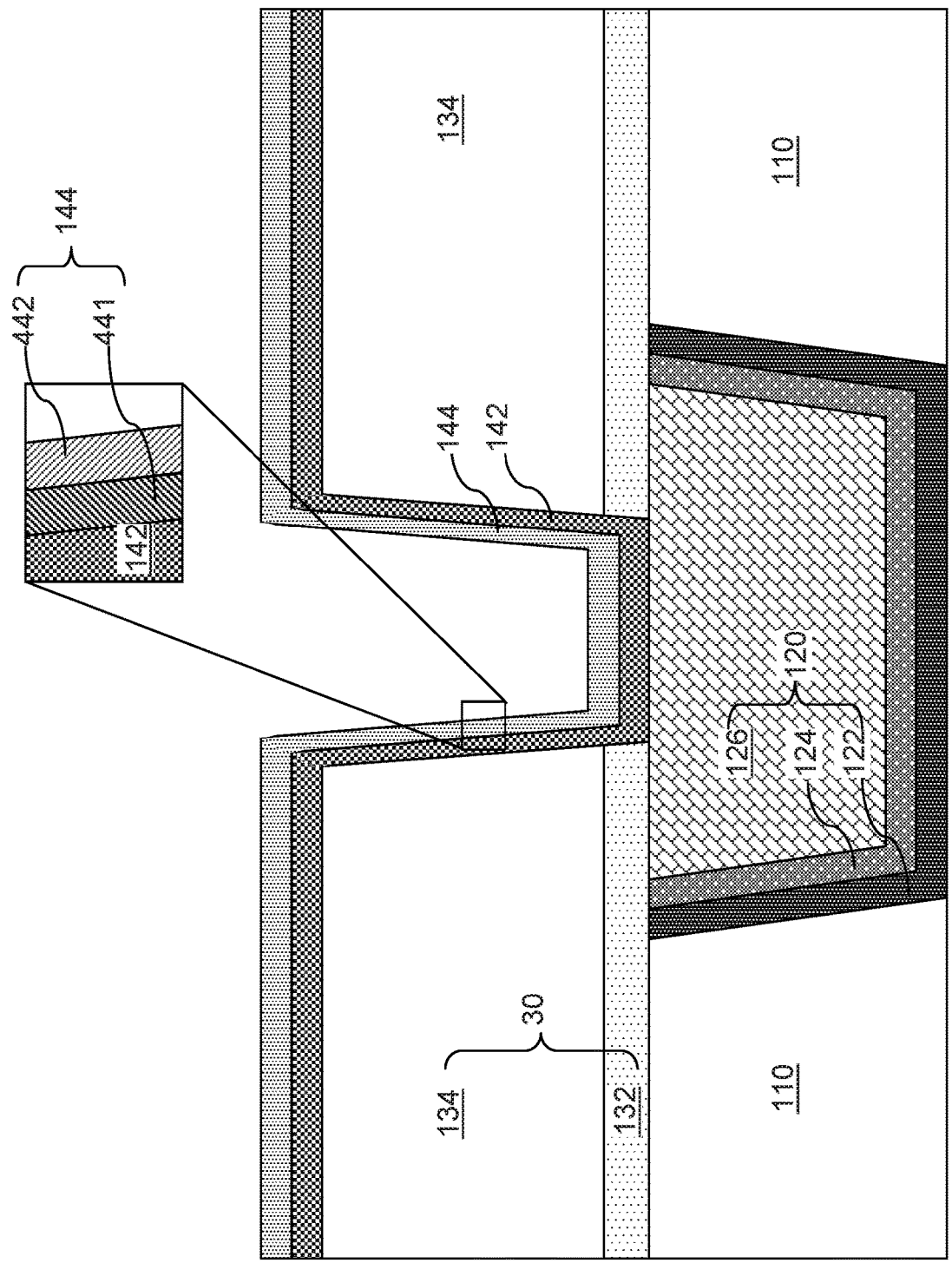
FIG. 5C is a vertical cross-sectional view of the portion of the exemplary structure after formation of a metallic adhesion layer having a third configuration according to an embodiment of the present disclosure.

Referring to FIG. 5C, a third configuration of the exemplary structure is illustrated, which includes a metallic adhesion layer 144 formed by deposition of a stack of a transition metal layer 441 and a copper layer 442. In this configuration, the transition metal layer 441 may be deposited first, and the copper layer 442 may be deposited on the transition metal layer 441. The transition metal layer 441 may have the same material composition as any of the transition metal layers (441, 441) in the first configuration of the exemplary structure illustrated in FIG. 5A. For example, the transition metal layer 441 may consist essentially of at least one transition metal such as at least one elemental metal selected from Co, Ru, Ta, Mo, and W. In one embodiment, the transition metal layer 441 consists essentially of a single transition metal selected from Co, Ru, Ta, Mo, and W. In another embodiment, the transition metal layer 441 may consist essentially of, an intermetallic alloy of at least two transition metal elements. For example, the intermetallic alloy may include, and/or may consist essentially of, an intermetallic alloy of Co, Ru, Ta, Mo, and/or W. In one embodiment, the transition metal layer 441 consists essentially of cobalt. The copper layer 442 consists essentially of copper.

The transition metal layer 441 may be formed by physical vapor deposition (sputtering), chemical vapor deposition, or atomic layer deposition. The copper layer 442 may be formed by physical vapor deposition (sputtering), chemical vapor deposition, or atomic layer deposition. The total thickness of the metallic adhesion layer 144, i.e., the sum of the thicknesses of the transition metal layer 441 and the copper layer 442, may be in a range from 0.5 nm to 10 nm, such as from 1 nm to 6 nm, although lesser and greater thicknesses may also be used. The thickness of the transition metal layer 441 may be about 1 monolayer, less than 1 monolayer, or more than 1 monolayer. The thickness of the copper layer 442 may be about 1 monolayer, less than 1 monolayer, or more than 1 monolayer.

The atoms of the transition metal layer 441 and the copper layer 442 interdiffuse naturally in embodiments in which one or more of the transition metal layer 441 and the copper layer 442 have a thickness of less than 1 monolayer. Additionally or alternatively, the atoms of the transition metal layer 441 and the copper layer 442 thermally interdiffuse during deposition of the transition metal layer 441 and/or during a subsequent thermal processing step. In embodiments in which the interdiffusion of the transition metal atoms and copper atoms from the transition metal layer 441 and the copper layer 442 is not complete, the metallic adhesion layer 144 may have a compositional modulation as a function of a distance from the metallic nitride liner 142. In other words, in embodiments in which the composition of the metallic nitride liner 142 is not completely homogenized through interdiffusion, the metallic adhesion layer 144 may have a compositional modulation as a function of a distance from the metallic nitride liner 142.

Optionally, interdiffusion among atoms of the transition metal layer 441 and the copper layer 442 may be enhanced by performing a plasma treatment process or a thermal anneal process. In one embodiment, enhancing compositional uniformity of a layer stack including the transition metal layer 441 and the copper layer 442 may be effectuated by performing a plasma treatment process on the layer stack. For example, a hydrogen plasma treatment process may be performed to increase the interdiffusion among atoms of the transition metal layer 441 and the copper layer 442. In one embodiment, enhancing compositional uniformity of the layer stack including the transition metal layer 441 and the copper layer 442 may be effectuated by performing a thermal anneal process.

Upon formation, and after the optional compositional homogenization process (if used), the metallic adhesion layer 144 may have a compositional modulation as a function of a distance from the metallic nitride liner 142, for example, as a function of a distance from an inner sidewall of the metallic nitride liner 142. In some embodiments, the position of a local peak atomic concentration of the at least one transition metal within the metallic adhesion layer 142 may be at an outer sidewall of the metallic adhesion layer 144 (such as an interface between the metallic nitride liner 142 and the metallic adhesion layer 144). In some embodiments, the atomic concentration of copper within the metallic adhesion layer 144 may have a local minimum at an outer sidewall of the metallic adhesion layer 144 (such as an interface between the metallic nitride liner 142 and the metallic adhesion layer 144).

In alternative embodiments, the metallic adhesion layer 144 may be completely homogenized so that the material composition of the metallic adhesion layer is the same throughout the entirety thereof.

Figure 5D:
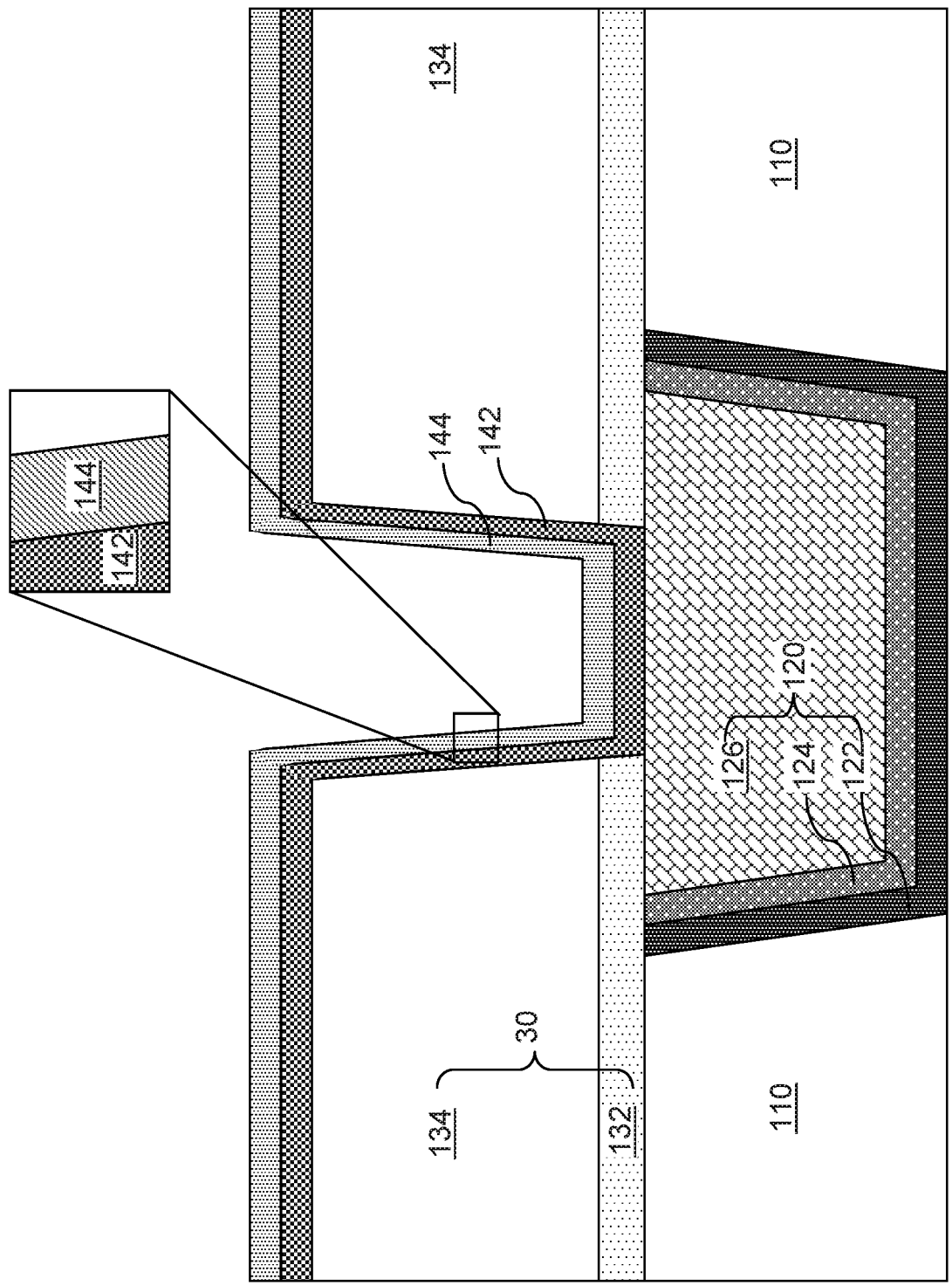
FIG. 5D is a vertical cross-sectional view of the portion of the exemplary structure after formation of a metallic adhesion layer having a fourth configuration according to an embodiment of the present disclosure.

Referring to FIG. 5D, a fourth configuration of the exemplary structure is illustrated, which includes a metallic adhesion layer 144 formed by a multi-metal deposition process. Copper atoms and atoms of the at least one transition metal are simultaneously deposited in the multi-metal deposition process to form the alloy of copper and the at least one transition metal with a uniform material composition throughout. In one embodiment, the at least one transition metal comprises, and/or consists of, at least one elemental metal selected from Co, Ru, Ta, Mo, and W. The at least one transition metal may consist of a single elemental metal selected from Co, Ru, Ta, Mo, and W, or may include two or more elemental metals selected from Co, Ru, Ta, Mo, and W. In one embodiment, the at least one transition metal may be cobalt.

In one embodiment, the multi-metal deposition process may include a chemical vapor deposition in which a copper-containing precursor gas and at least one transition-metal-containing precursor gas are simultaneously flowed into a process chamber including the exemplary structure at an elevated temperature. The chemical vapor deposition process may be a thermal chemical vapor deposition process in which the copper-containing precursor gas and the at least one transition-metal-containing precursor gas are thermally decomposed. Alternatively, the chemical vapor deposition process may be a plasma-enhanced chemical vapor deposition (PECVD) process in which the copper-containing precursor gas and the at least one transition-metal-containing precursor gas are decomposed with the assistance of plasma energy. Generally, any combination of a copper-containing precursor gas and at least one transition-metal-containing precursor gas may be used provided that an alloy of copper and the at least one transition metal element may be formed with a target composition, in which copper has an atomic percentage in a range from 10% to 90% such as from 20% to 80%, and the at least one transition metal element has an atomic percentage in a range from 90% to 10% such as from 80% to 20%. The alloy of copper and the at least one transition metal element may consist essentially of copper and the at least one transition metal element.

In another embodiment, the multi-metal deposition process may include a physical vapor deposition in which copper and at least one transition metal element are sputtered simultaneously. In one embodiment, a single sputtering target including an alloy of copper and the at least one transition metal element may be used during the multi-metal deposition process. Alternatively, a sputtering target including copper and another sputtering target including the at least one transition metal element may be used as dual targets during the multi-metal deposition process, and both of the two targets may be sputtered simultaneously or alternately. In one embodiment, the alloy of copper and the at least one transition metal element may include copper an atomic percentage in a range from 10% to 90% such as from 20% to 80%, and include the at least one transition metal element an atomic percentage in a range from 90% to 10% such as from 80% to 20%. The alloy of copper and the at least one transition metal element may consist essentially of copper and the at least one transition metal element.

In yet another embodiment, the multi-metal deposition process may include an atomic layer deposition in which a copper-containing precursor gas and at least one transition-metal-containing precursor gas are alternately flowed into a process chamber including the exemplary structure at an elevated temperature. The atomic layer deposition process may be a thermally activated deposition process in which the copper-containing precursor gas and the at least one transition-metal-containing precursor gas are thermally decomposed. Alternatively, the atomic layer deposition process may be a plasma-assisted atomic layer deposition process in which at least one of the copper-containing precursor gas and the at least one transition-metal-containing precursor gas is decomposed with the assistance of plasma energy. The copper atoms and the atoms of the at least one transition metal may be intermixed at an atomic level to provide a homogeneous alloy of copper and the at least one transition metal. Generally, any combination of a copper-containing precursor gas and at least one transition-metal-containing precursor gas may be used provided that an alloy of copper and the at least one transition metal element may be formed with a target composition, in which copper has an atomic percentage in a range from 10% to 90% such as from 20% to 80%, and the at least one transition metal element has an atomic percentage in a range from 90% to 10% such as from 80% to 20%. The alloy of copper and the at least one transition metal element may consist essentially of copper and the at least one transition metal element.

The thickness of the metallic adhesion layer 144 as measured on a sidewall of the metallic nitride liner 142 may be in a range from 0.5 nm to 10 nm, such as from 1 nm to 6 nm, although lesser and greater thicknesses may also be used. In embodiments in which the copper layers and the layers of the at least one transition metal element are not homogeneously intermixed, the metallic adhesion layer 144 may have a compositional modulation along the thickness direction, and the structure illustrated in FIG. 5A may be provided.

Figure 6:
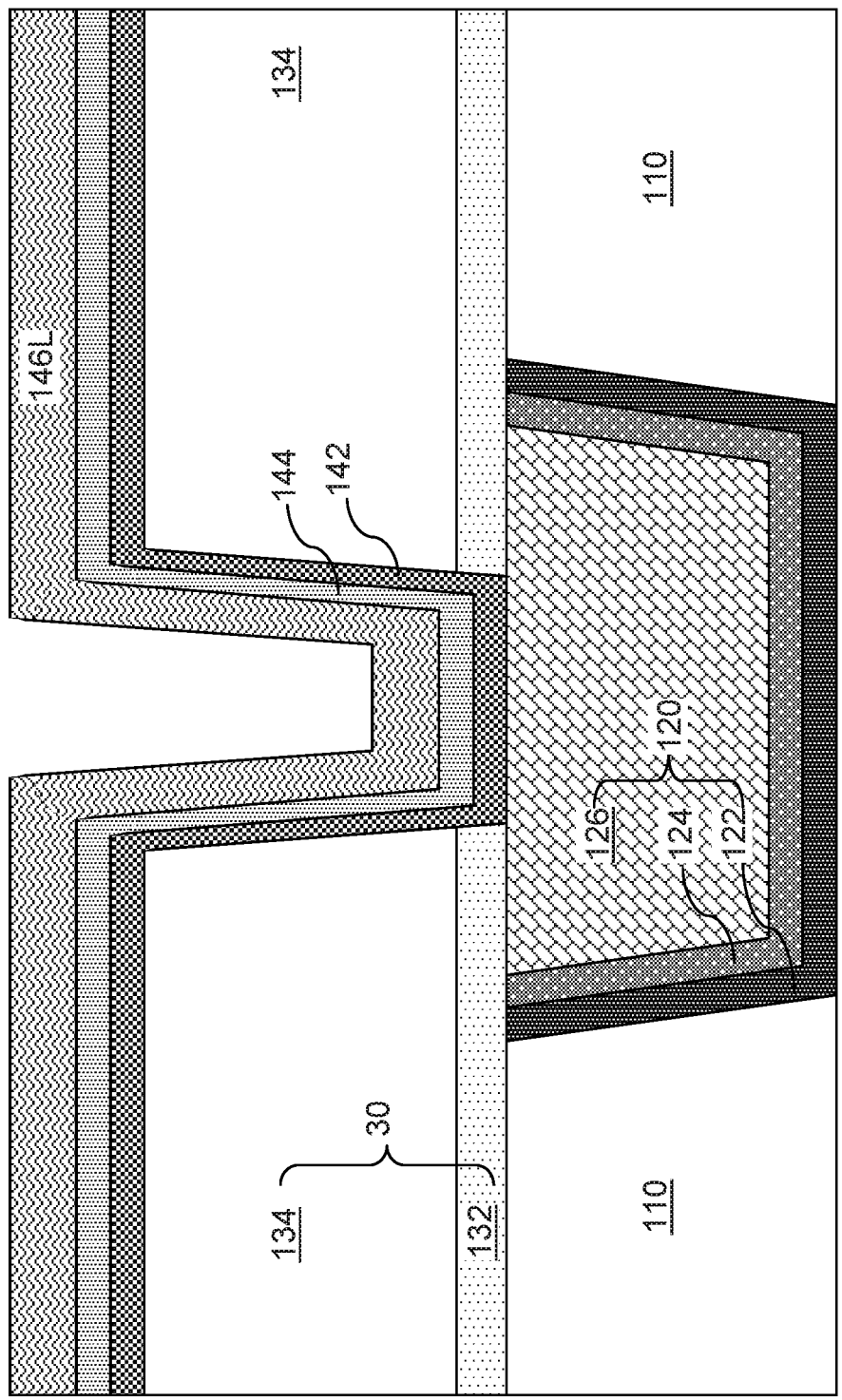
FIG. 6 is a vertical cross-sectional view of the portion of the exemplary structure after deposition of a first copper fill material layer according to an embodiment of the present disclosure.

Referring to FIG. 6, a first copper fill material layer 146L consisting essentially of copper may be formed on the physically exposed surfaces of the metallic adhesion layer 144. The first copper fill material layer 146L may be formed by physical vapor deposition, electroplating, or a combination of a physical vapor deposition process that forms a copper seed layer and an electroplating process that electroplates copper on the copper seed layer. In embodiments in which a copper seed layer is used, the thickness of the copper seed layer on the sidewalls of the metallic adhesion layer may be in a range from 1 nm to 20 nm, such as from 2 nm to 10 nm, although lesser and greater thicknesses may also be used.

In one embodiment, the total thickness of the first copper fill material layer 146L may be selected such that a reflowed portion of the first copper fill material layer 146L after a subsequent reflow process does not completely fill the entirety of the volume that is laterally enclosed by the metallic adhesion layer 144 in the opening 131. Alternatively, the total thickness of the first copper fill material layer 146L may be selected such that a reflowed portion of the first copper fill material layer 146L completely fills the entirety of the volume that is laterally enclosed by the metallic adhesion layer 144 in the opening 131. In embodiments in which the aspect ratio of the opening 131 is not high enough (such as less than 2) so that the first copper fill material layer 146L may completely fill the entirety of the volume that is laterally enclosed by the metallic adhesion layer 144 in the opening 131, the thickness of the first copper fill material layer 146L may be selected such that the first copper fill material layer 146L fills the entirety of the volume laterally enclosed by the metallic adhesion layer 144 in the opening 131 without a reflow process. The embodiment illustrated in FIG. 6 corresponds to the embodiment in which a reflowed portion of the first copper fill material layer 146L after a subsequent reflow process does not completely fill the entirety of the volume that is laterally enclosed by the metallic adhesion layer 144 in the opening 131.

Figure 7:
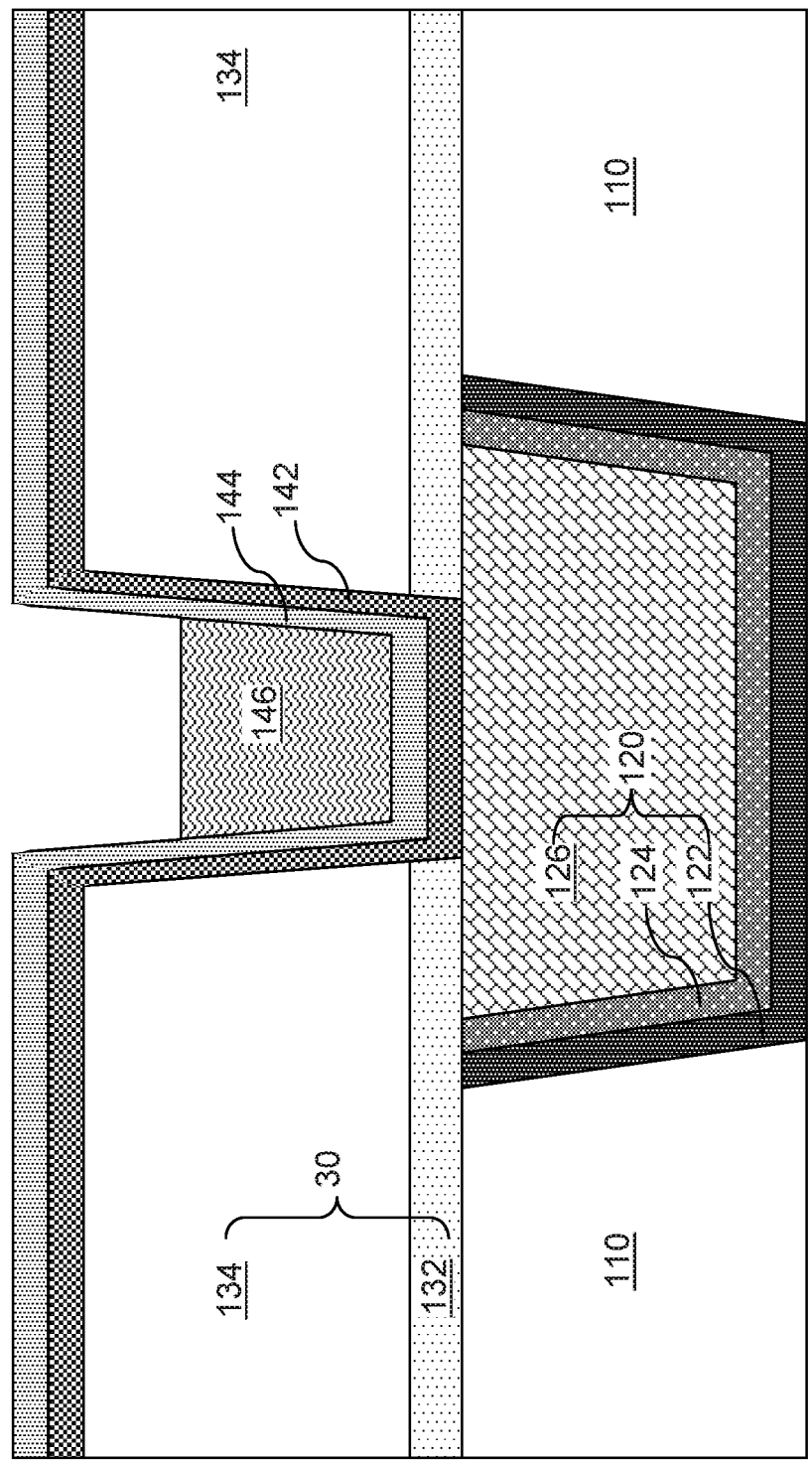
FIG. 7 is a vertical cross-sectional view of the portion of the exemplary structure after formation of a first copper fill material portion by reflow of the first copper fill material layer according to an embodiment of the present disclosure.

Referring to FIG. 7, the exemplary structure may be annealed at an elevated temperature to induce reflow of copper in the first copper fill material layer 146L. This anneal process is herein referred to as a reflow anneal process. A first copper fill material portion 146 may be formed within the volume that is laterally enclosed by the metallic adhesion layer 144 in the opening 131 by reflow of the first copper fill material layer 146L. The elevated temperature may be in a range from 300 degrees Celsius to 400 degrees Celsius, such as from 350 degrees Celsius to 400 degrees Celsius. A hydrogen-containing ambient may be used assist reflow of copper during the reflow anneal process.

In one embodiment, the reflow anneal process may be performed within the temperature range from 300 degrees Celsius to 400 degrees Celsius in the presence of atomic hydrogen. In one embodiment, atomic hydrogen may be generated using a microwave-excitation high density plasma apparatus, which may generate a plasma of a mixture of an inert gas and hydrogen. For example, a plasma of a mixture of krypton atoms and hydrogen atoms may be used. The atomic hydrogen enhances reflow of copper in the first copper fill material portion 146 into unfilled volumes of the openings 131 that are laterally enclosed by a respective vertically-extending portion of the metallic adhesion layer 144. The hydrogen plasma during the reflow anneal process may reduce the copper reflow temperature by about 100 degrees Celsius, thereby lowering the reflow temperature below 400 degrees Celsius and avoiding decomposition of low-k dielectric materials in the dielectric material layers illustrated in FIG. 1. The duration of the plasma during the reflow anneal process may be in a range from 3 second to 600 seconds, such as from 10 seconds to 100 seconds. The duration of the plasma during the reflow anneal process may vary depending on the elevated temperature at which the reflow anneal process is performed.

Referring back to FIG. 7, the reflow anneal process may remove voids at lower portions of the openings 131 even in embodiments in which the openings 131 have a high aspect ratio (such as an aspect ratio greater than 3). The chamber pressure while the plasma is present may be about 1 Torr. The atomic percentage of hydrogen atoms within the plasma of the mixture of hydrogen and the inert gas may be in a range from 2% to 50%, such as from 5% to 20%, although lesser and higher atomic percentages may also be used.

The first copper fill material portion 146 may be formed on an inner sidewall of the metallic adhesion layer 144. The first copper fill material portion 146 may be a reflowed portion of the first copper fill material layer 146L that reflows into an unfilled volume of the illustrated opening 131 through the dielectric material layer 134. In one embodiment, the topmost surface of the first copper fill material portion 146 may be formed underneath the horizontal plane including the top surface of the dielectric material layer 134. In other words, an unfilled cavity may be present between the top surface of the first copper fill material portion 146 and the horizontal plane including the top surface of the dielectric material layer 134.

Figure 8:
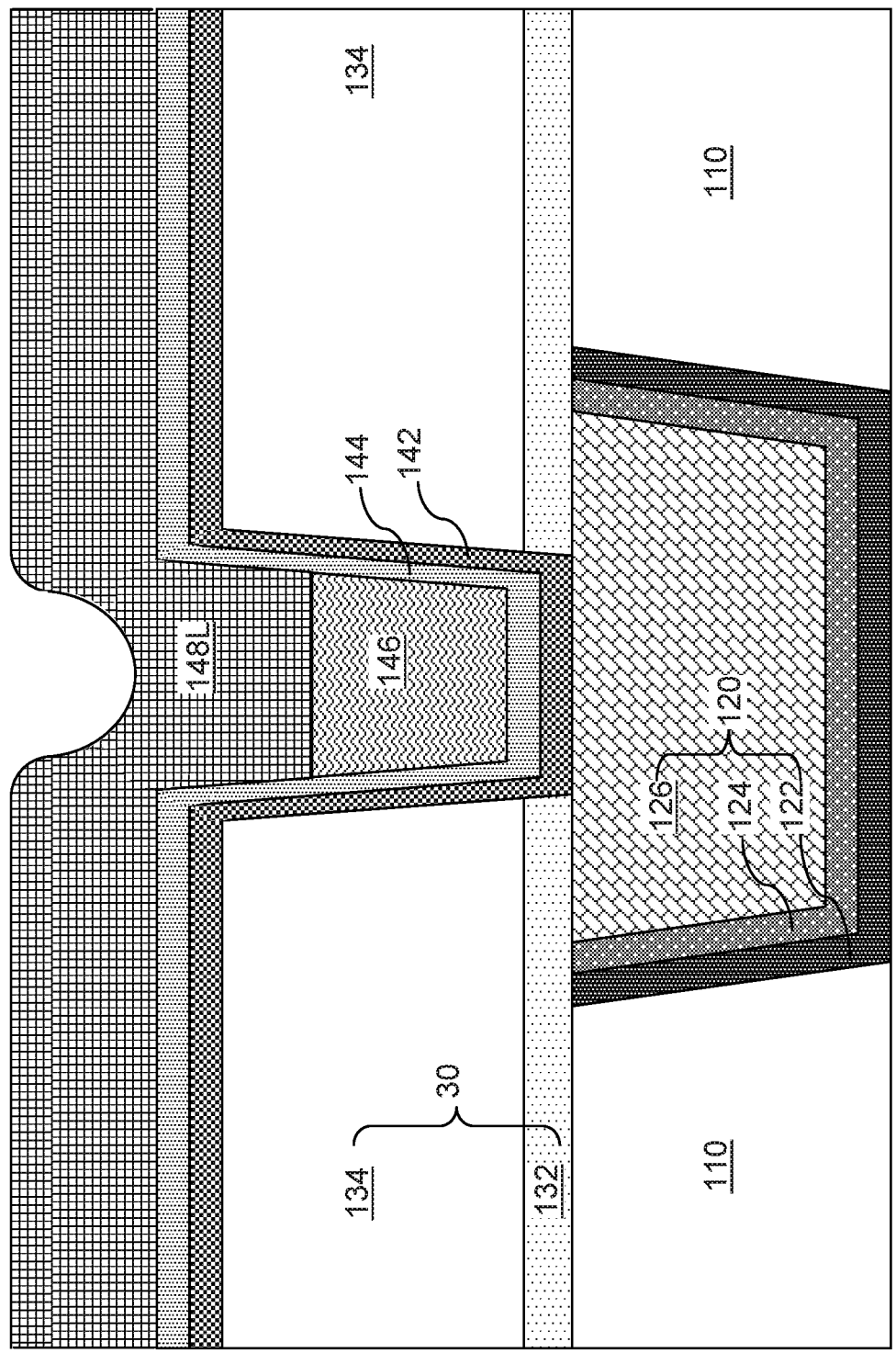
FIG. 8 is a vertical cross-sectional view of the portion of the exemplary structure after formation of a second copper fill material layer according to an embodiment of the present disclosure.

Referring to FIG. 8, a second copper fill material layer 148L consisting essentially of copper may be deposited over the first copper fill material portion 146 and over the physically exposed surfaces of the metallic adhesion layer 144. The second copper fill material layer 148L may be formed by physical vapor deposition, electroplating, or a combination of a physical vapor deposition process that forms a copper seed layer and an electroplating process that electroplates copper on the copper seed layer. In embodiments in which a copper seed layer is used, the thickness of the copper seed layer on the sidewalls of the metallic adhesion layer may be in a range from 1 nm to 20 nm, such as from 2 nm to 10 nm, although lesser and greater thicknesses may also be used. The thickness of the second copper fill material layer 148L may be selected such that the entire volume of each opening 131 through the dielectric material layer 134 is completely filled with the metallic nitride liner 142, the metallic adhesion layer 144, a respective first copper fill material portion 146, and the second copper fill material layer 148L.

Figure 9A:
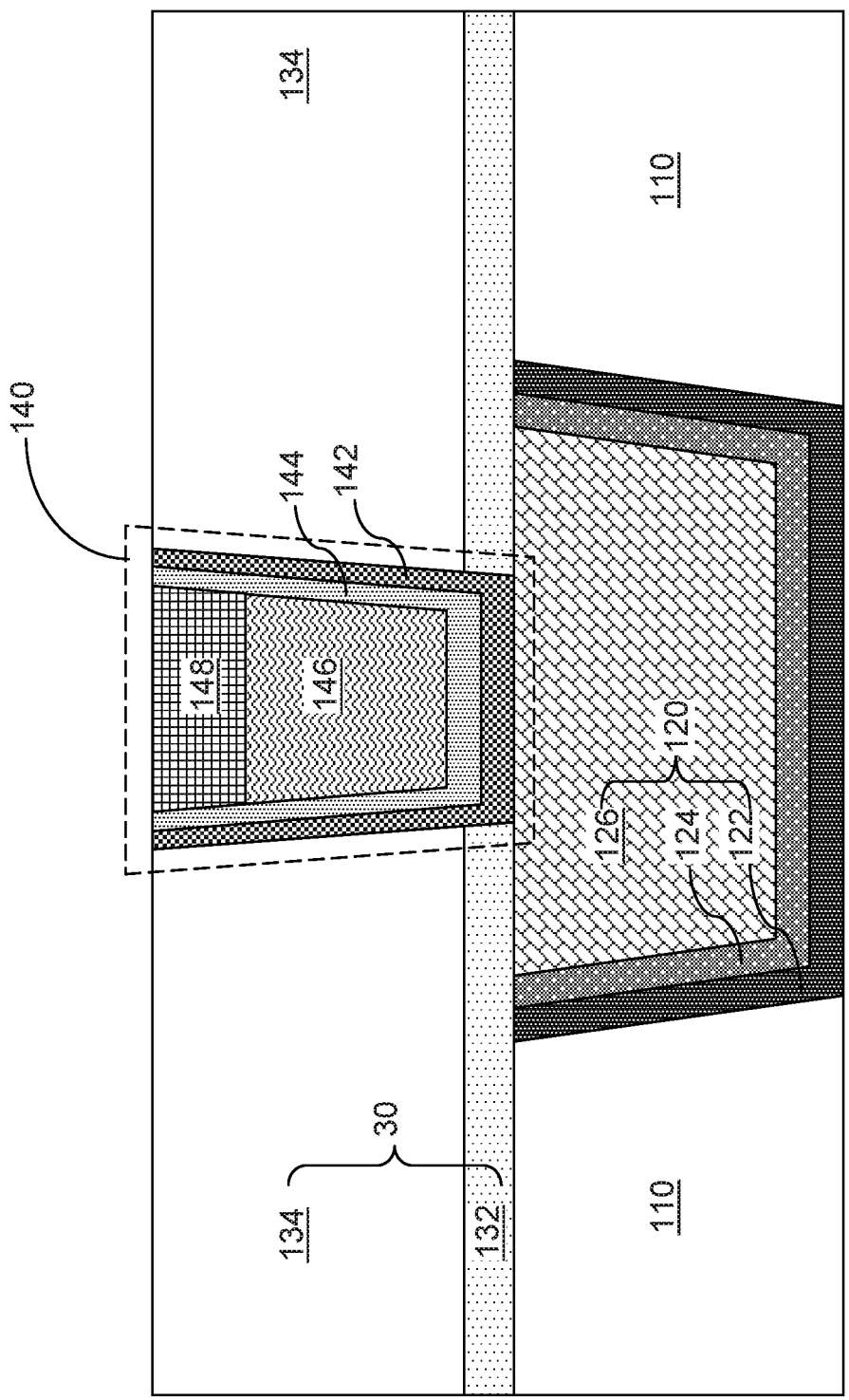
FIG. 9A is a vertical cross-sectional view of the portion of the exemplary structure after formation of a metal interconnect structure by removal of excess portions of conductive materials above the top surface of the dielectric material layer according to an embodiment of the present disclosure.

Referring to FIG. 9A, a planarization process may be performed to remove excess portions of the metallic nitride liner 142, the metallic adhesion layer 144, and the second copper fill material layer 148L that are located above the horizontal plane including the top surface of the dielectric material layer 134. For example, a chemical mechanical planarization process may be performed to polish the portion of the second copper fill material layer 148L using the metallic adhesion layer 144 and/or the metallic nitride liner 142 as a stopping layer. A touch-up polish process may be subsequently performed to remove horizontal portions of the metallic nitride liner 142 and the metallic adhesion layer 144 and to remove a portion of the second copper fill material layer 148L overlying the horizontal plane including the top surface of the dielectric material layer 134.

Each set of material portions that fills a respective one of the openings 131 through the dielectric material layer 134 constitutes a metal interconnect structure 140. Each metal interconnect structure 140 includes a metallic nitride liner 142 (which is a patterned portion of the metallic nitride liner 142 as formed at the processing steps of FIG. 4), a metallic adhesion layer 144 (which is a patterned portion of the metallic adhesion layer 144 as formed at the processing steps of FIG. 5A, FIG. 5B, FIG. 5C, or FIG. 5D), a first copper fill material portion 146 (as formed at the processing steps of FIG. 7), and a second copper fill material portion 148, which is a remaining portion of the second copper fill material layer 148L after the planarization process. Each metal interconnect structure 140 may be a metal via structure, a metal line structure, or an integrated line and via structure.

The configuration illustrated in FIG. 9A corresponds to an embodiment in which the metal interconnect structure is a metal via structure. In such an embodiment, the underlying conductive material portion 120 may be a metal line structure or an integrated line and via structure.

Figure 9B:
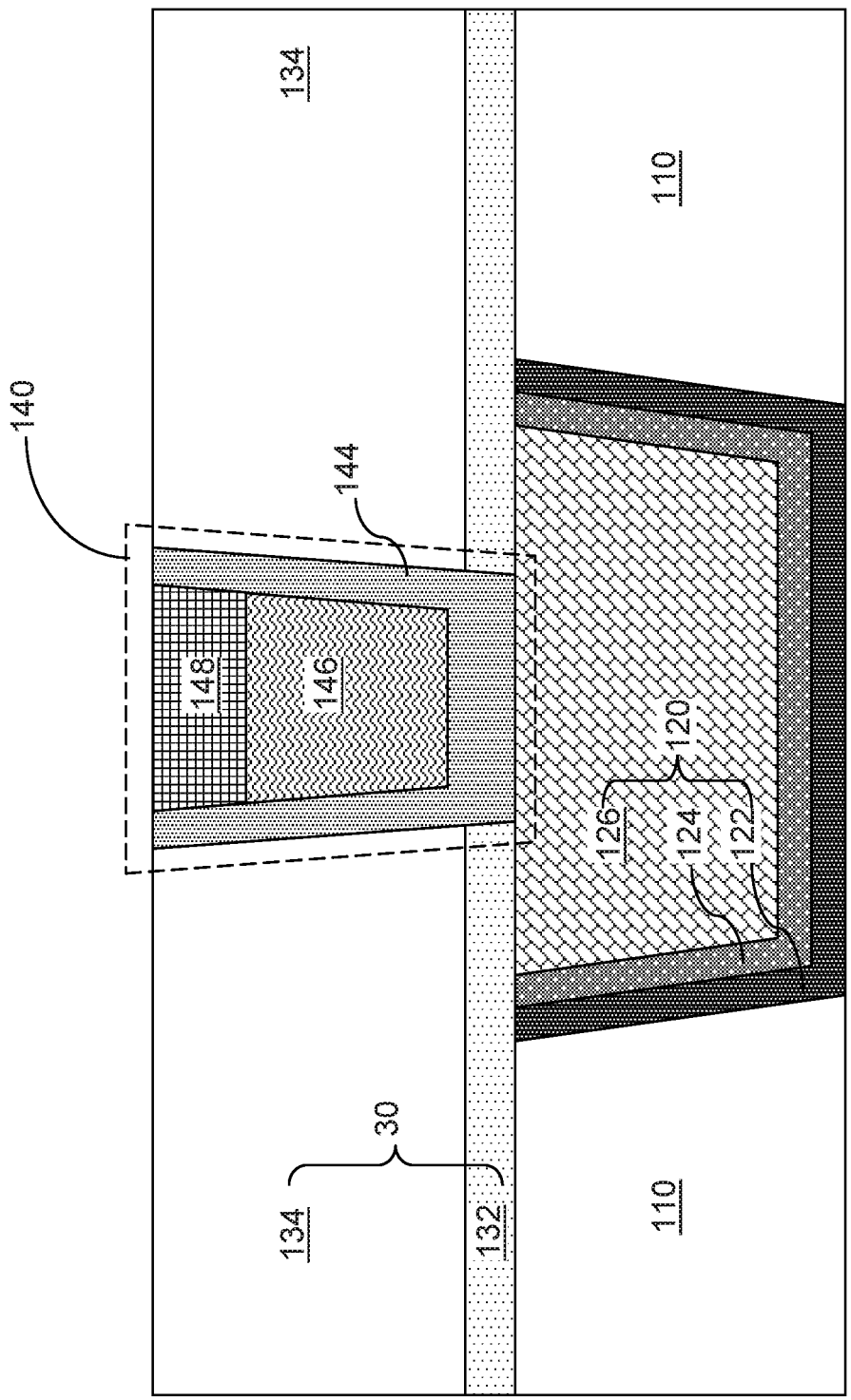
FIG. 9B is a vertical cross-sectional view of another configuration of the exemplary structure of FIG. 9A derived by omission of the metallic nitride liner according to an embodiment of the present disclosure.
Figure 12A:
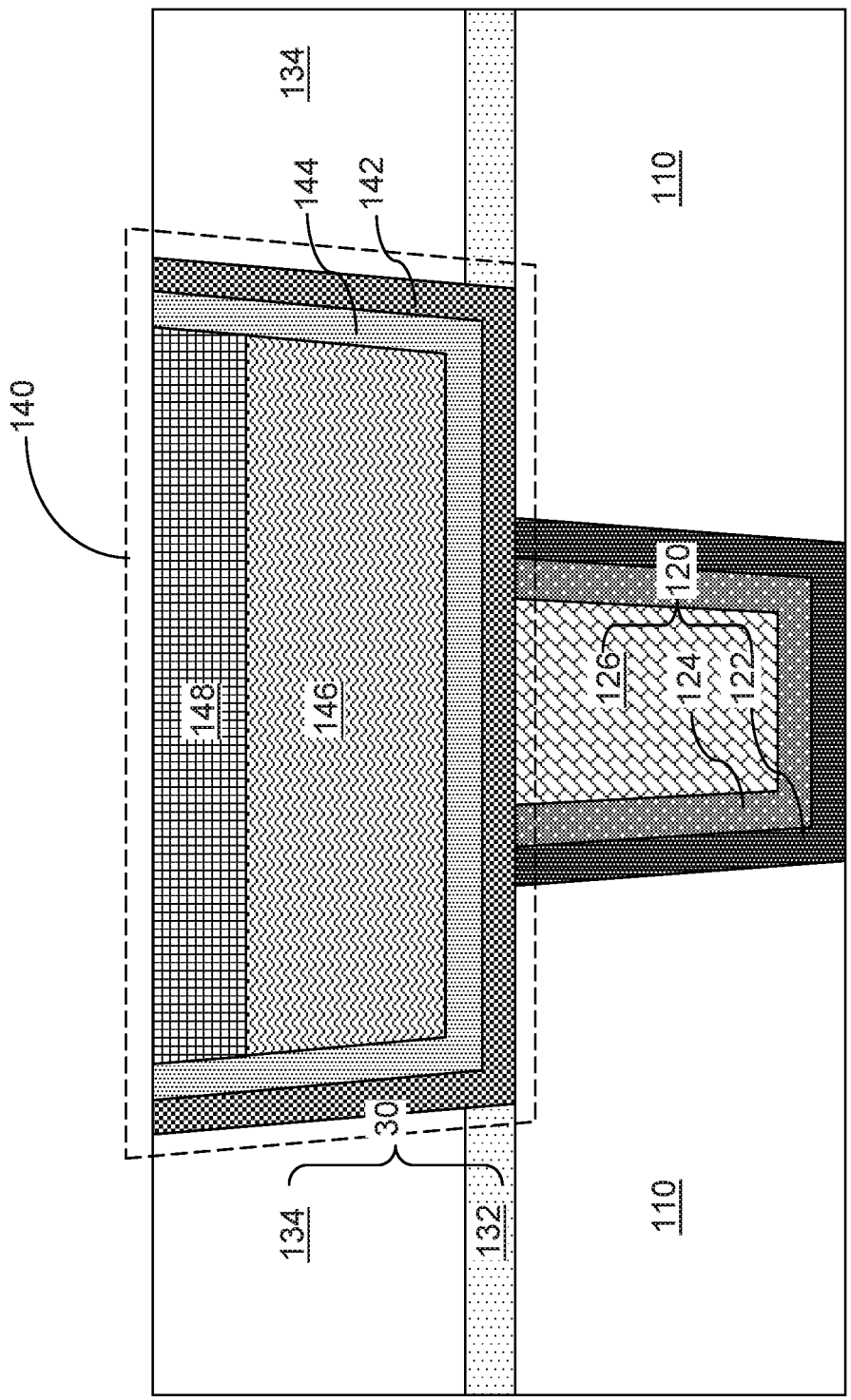
FIG. 12A is a vertical cross-sectional view of a portion of a second alternative embodiment of the exemplary structure after formation of a metal interconnect structure according to an embodiment of the present disclosure.

FIG. 9B illustrates another configuration of the exemplary structure of FIG. 12A, which can be derived from the exemplary structure of FIG. 9A by omission of the metallic nitride liner 142 according to an embodiment of the present disclosure.

Figure 10:
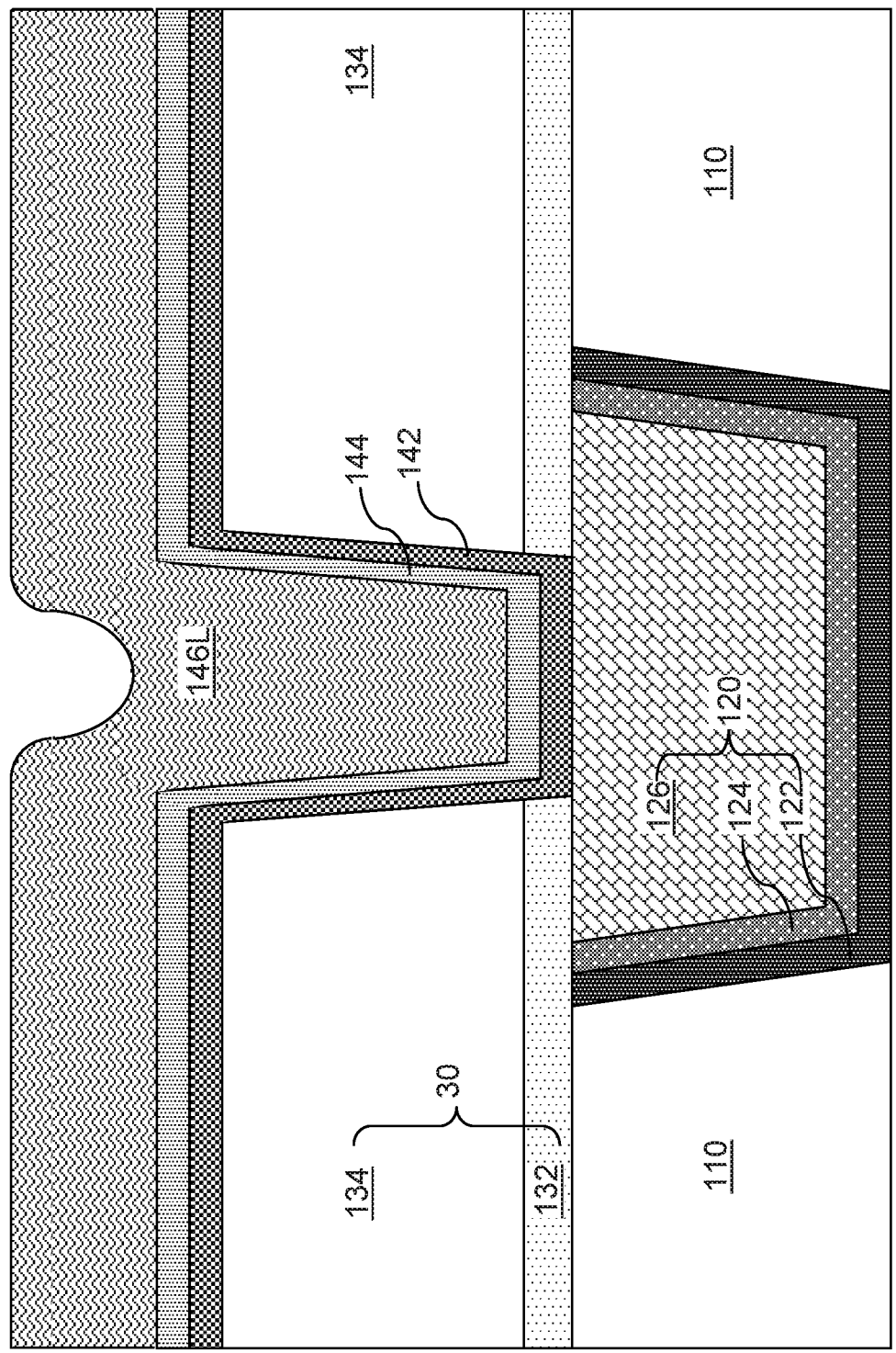
FIG. 10 is a vertical cross-sectional view of the portion of a first alternative embodiment of the exemplary structure after formation of a first copper fill material layer according to an embodiment of the present disclosure.

Referring to FIG. 10, a first alternative embodiment of the exemplary structure may be derived from the exemplary structure of FIG. 6 by increasing the thickness of the first copper fill material layer 146L. In such an embodiment, the total thickness of the first copper fill material layer 146L may be selected such that a reflowed portion of the first copper fill material layer 146L completely fills the entirety of the volume that is laterally enclosed by the metallic adhesion layer 144 in the opening 131. In embodiments in which the aspect ratio of the opening 131 is not high enough (such as less than 2) so that the first copper fill material layer 146L may completely fill the entirety of the volume that is laterally enclosed by the metallic adhesion layer 144 in the opening 131, the thickness of the first copper fill material layer 146L may be selected such that the first copper fill material layer 146L fills the entirety of the volume laterally enclosed by the metallic adhesion layer 144 in the opening 131 without a reflow process.

Optionally, a reflow anneal process described above may be performed to remove any void within the volume of each opening 131 through the dielectric material layer 134.

Figure 11A:
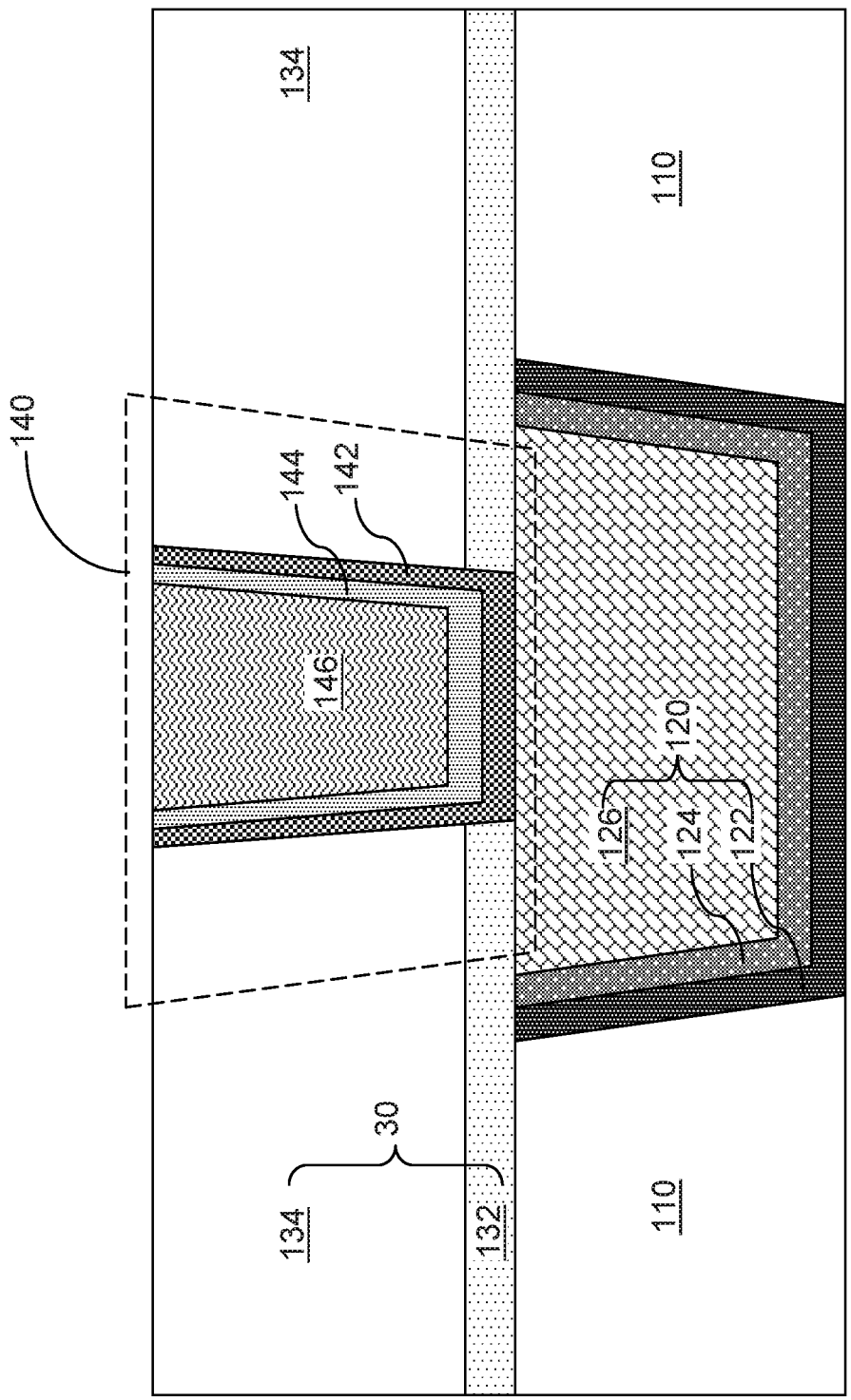
FIG. 11A is a vertical cross-sectional view of the portion of the first alternative embodiment of the exemplary structure after formation of a metal interconnect structure by removal of excess portions of conductive materials above the top surface of the dielectric material layer according to an embodiment of the present disclosure.

Referring to FIG. 11A, a planarization process may be performed to remove excess portions of the metallic nitride liner 142, the metallic adhesion layer 144, and the first copper fill material layer 146L that are located above the horizontal plane including the top surface of the dielectric material layer 134. For example, a chemical mechanical planarization process may be performed to polish the portion of the first copper fill material layer 146L using the metallic adhesion layer 144 and/or the metallic nitride liner 142 as a stopping layer. A touch-up polish process may be subsequently performed to remove horizontal portions of the metallic nitride liner 142 and the metallic adhesion layer 144 and to remove a portion of the first copper fill material layer 146L overlying the horizontal plane including the top surface of the dielectric material layer 134.

Each set of material portions that fills a respective one of the openings 131 through the dielectric material layer 134 constitutes a metal interconnect structure 140. Each metal interconnect structure 140 includes a metallic nitride liner 142 (which is a patterned portion of the metallic nitride liner 142 as formed at the processing steps of FIG. 4), a metallic adhesion layer 144 (which is a patterned portion of the metallic adhesion layer 144 as formed at the processing steps of FIG. 5A, FIG. 5B, FIG. 5C, or FIG. 5D), a first copper fill material portion 146, which is a remaining portion of the first copper fill material layer 146L after the planarization process. Each metal interconnect structure 140 may be a metal via structure, a metal line structure, or an integrated line and via structure.

The configuration illustrated in FIG. 11A corresponds to an embodiment in which the metal interconnect structure is a metal via structure. In this embodiment, the underlying conductive material portion 120 may be a metal line structure or an integrated line and via structure.

Figure 11B:
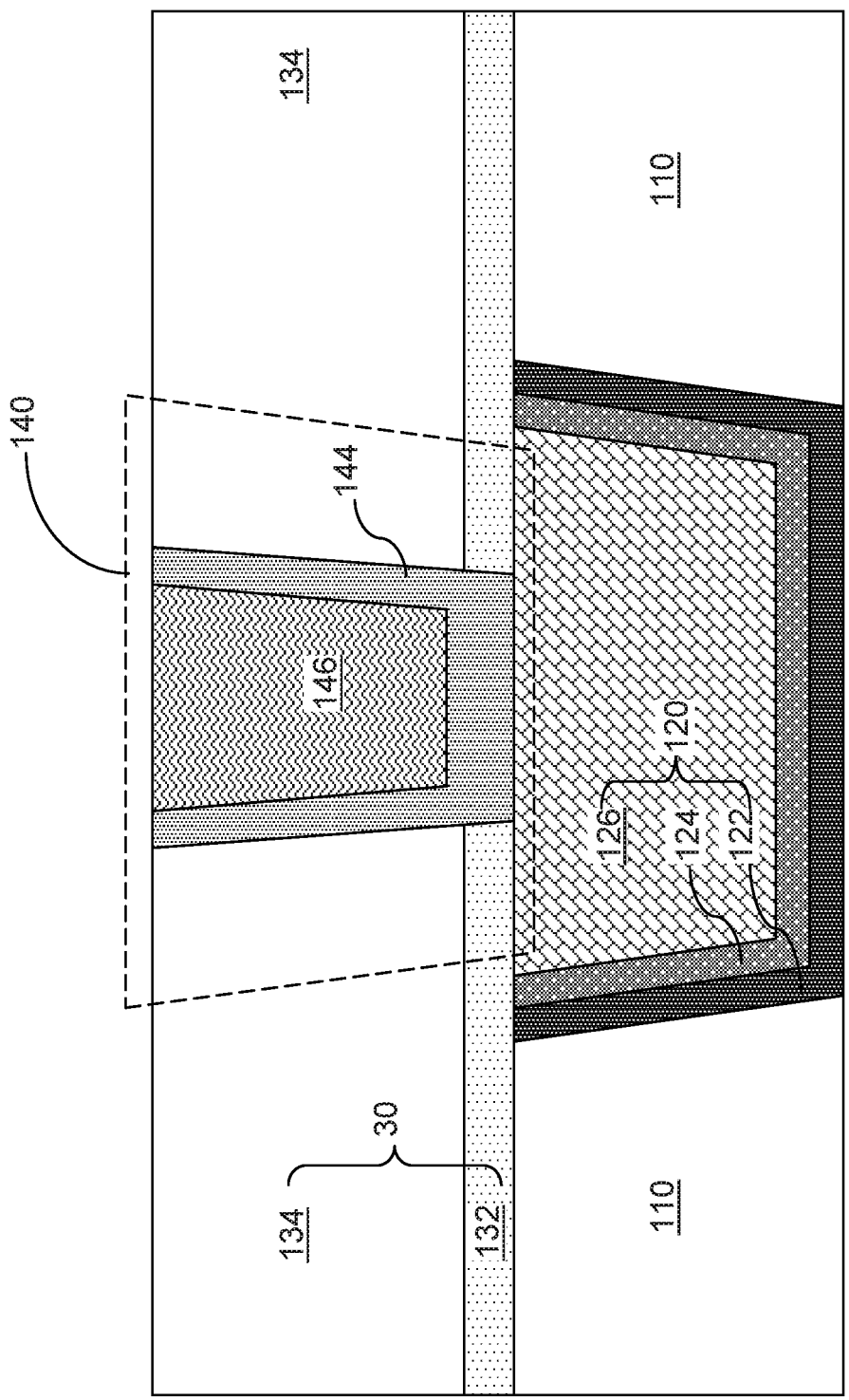
FIG. 11B is a vertical cross-sectional view of another configuration of the exemplary structure of FIG. 11A derived by omission of the metallic nitride liner according to an embodiment of the present disclosure.

FIG. 11B illustrates another configuration of the exemplary structure of FIG. 11A, which can be derived from the exemplary structure of FIG. 11A by omission of the metallic nitride liner 142 according to an embodiment of the present disclosure.

Referring to FIG. 12A, a second alternative embodiment of the exemplary structure may be derived from the exemplary structure of FIG. 9A by forming the opening 131 as a line cavity. In this embodiment, the metal interconnect structure 140 may be formed as a metal line structure, and the underlying conductive material portion 120 may be a metal via structure.

Figure 12B:
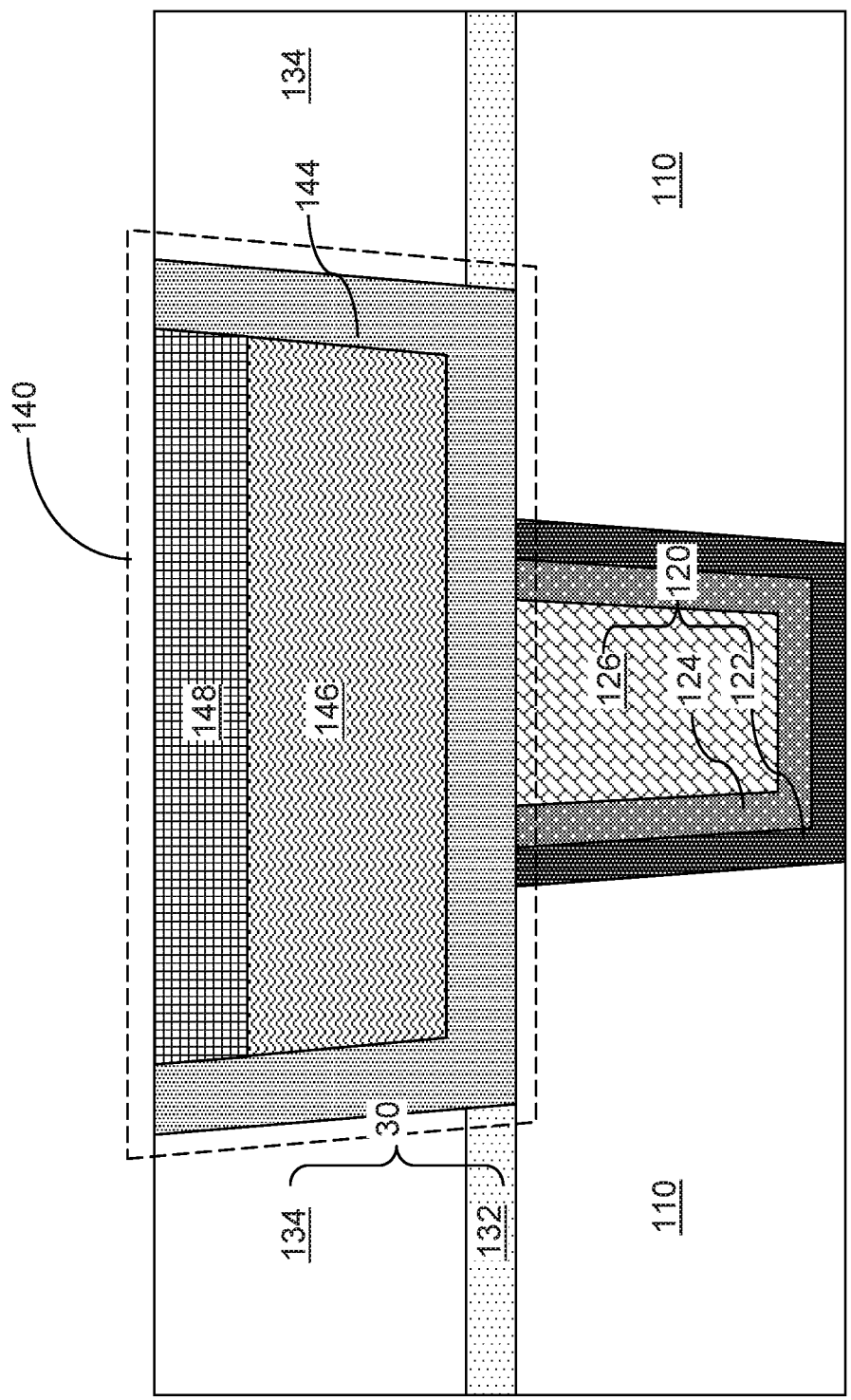
FIG. 12B is a vertical cross-sectional view of another configuration of the exemplary structure of FIG. 12A derived by omission of the metallic nitride liner according to an embodiment of the present disclosure.

FIG. 12B illustrates another configuration of the exemplary structure of FIG. 12A, which can be derived from the exemplary structure of FIG. 12A by omission of the metallic nitride liner 142 according to an embodiment of the present disclosure.

Referring to FIG. 13A, a third alternative embodiment of the exemplary structure may be derived from the first alternative embodiment of the exemplary structure of FIG. 11A by forming the opening 131 as a line cavity. In this embodiment, the metal interconnect structure 140 may be formed as a metal line structure, and the underlying conductive material portion 120 may be a metal via structure.

Figure 13B:
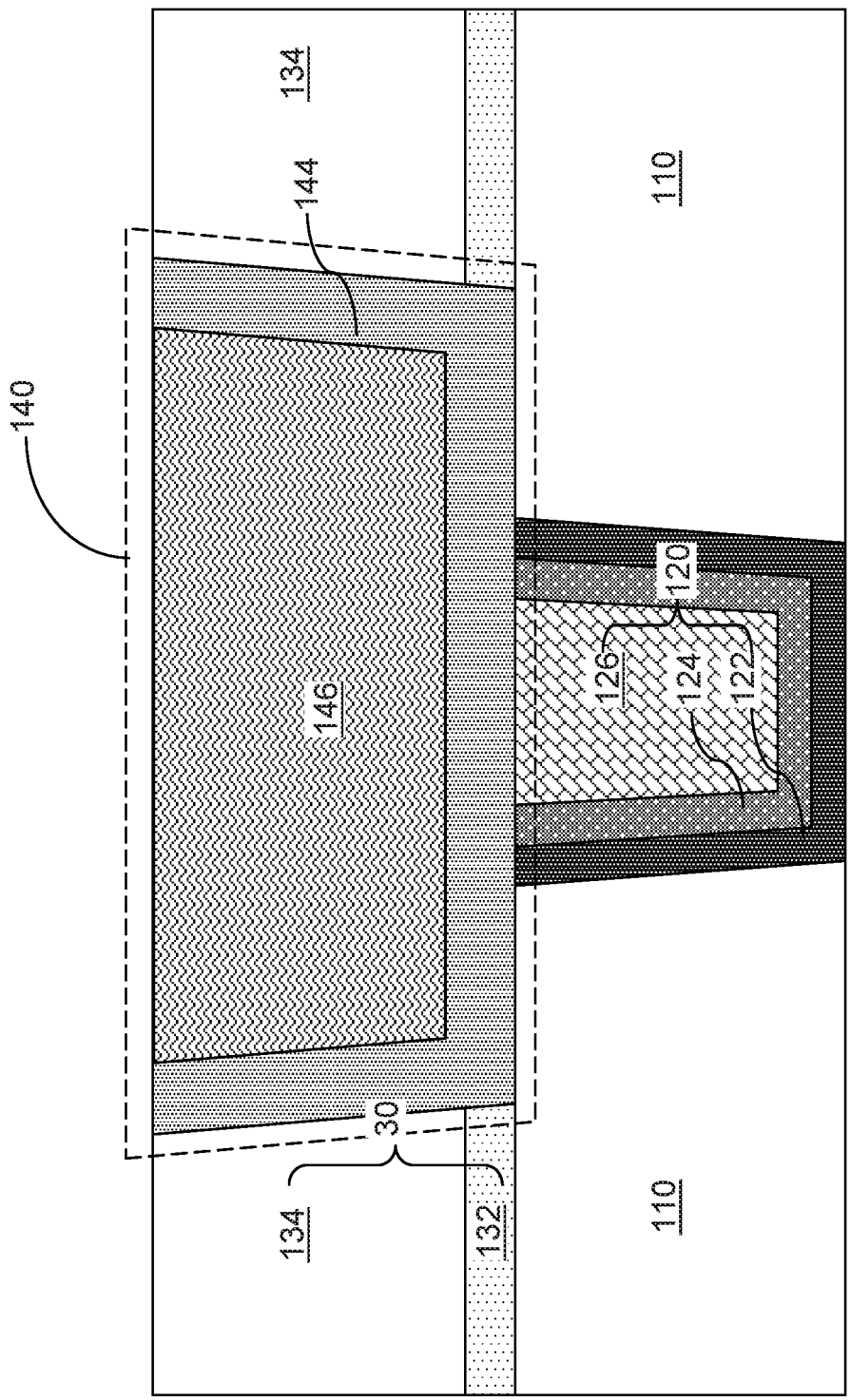
FIG. 13B is a vertical cross-sectional view of another configuration of the exemplary structure of FIG. 13A derived by omission of the metallic nitride liner according to an embodiment of the present disclosure.

FIG. 13B illustrates another configuration of the exemplary structure of FIG. 13A, which can be derived from the exemplary structure of FIG. 13A by omission of the metallic nitride liner 142 according to an embodiment of the present disclosure.

Referring to FIG. 14A, a fourth alternative embodiment of the exemplary structure may be derived from the exemplary structure of FIG. 9A by forming the opening 131 as an integrated line and via cavity. In this embodiment, the metal interconnect structure 140 may be formed as an integrated line and structure including a metal line and at least one metal via structure, and the underlying conductive material portion 120 may be a metal line structure or an integrated line and via structure.

Figure 14B:
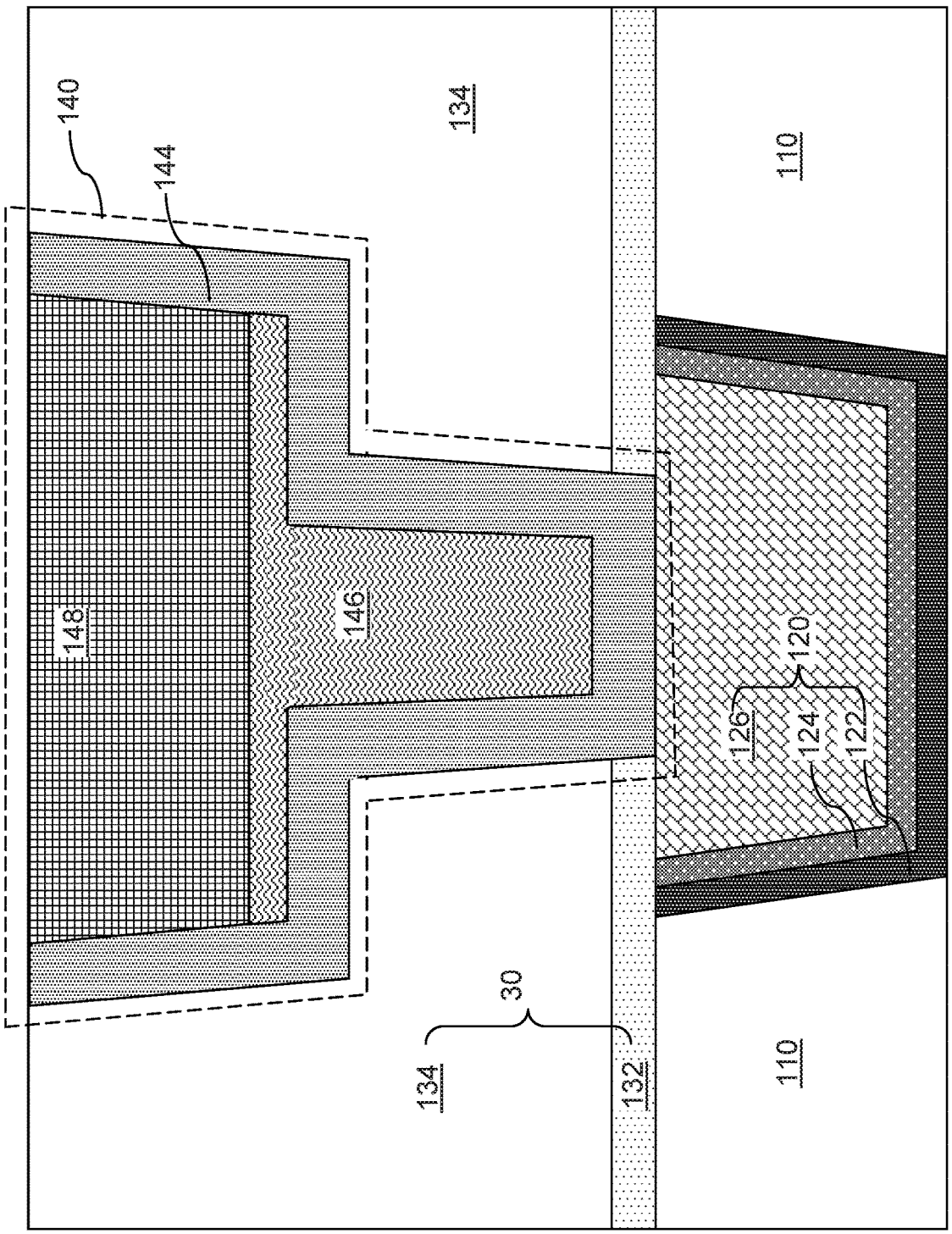
FIG. 14B is a vertical cross-sectional view of another configuration of the exemplary structure of FIG. 14A derived by omission of the metallic nitride liner according to an embodiment of the present disclosure.

FIG. 14B illustrates another configuration of the exemplary structure of FIG. 14A, which can be derived from the exemplary structure of FIG. 14A by omission of the metallic nitride liner 142 according to an embodiment of the present disclosure.

Figure 15A:
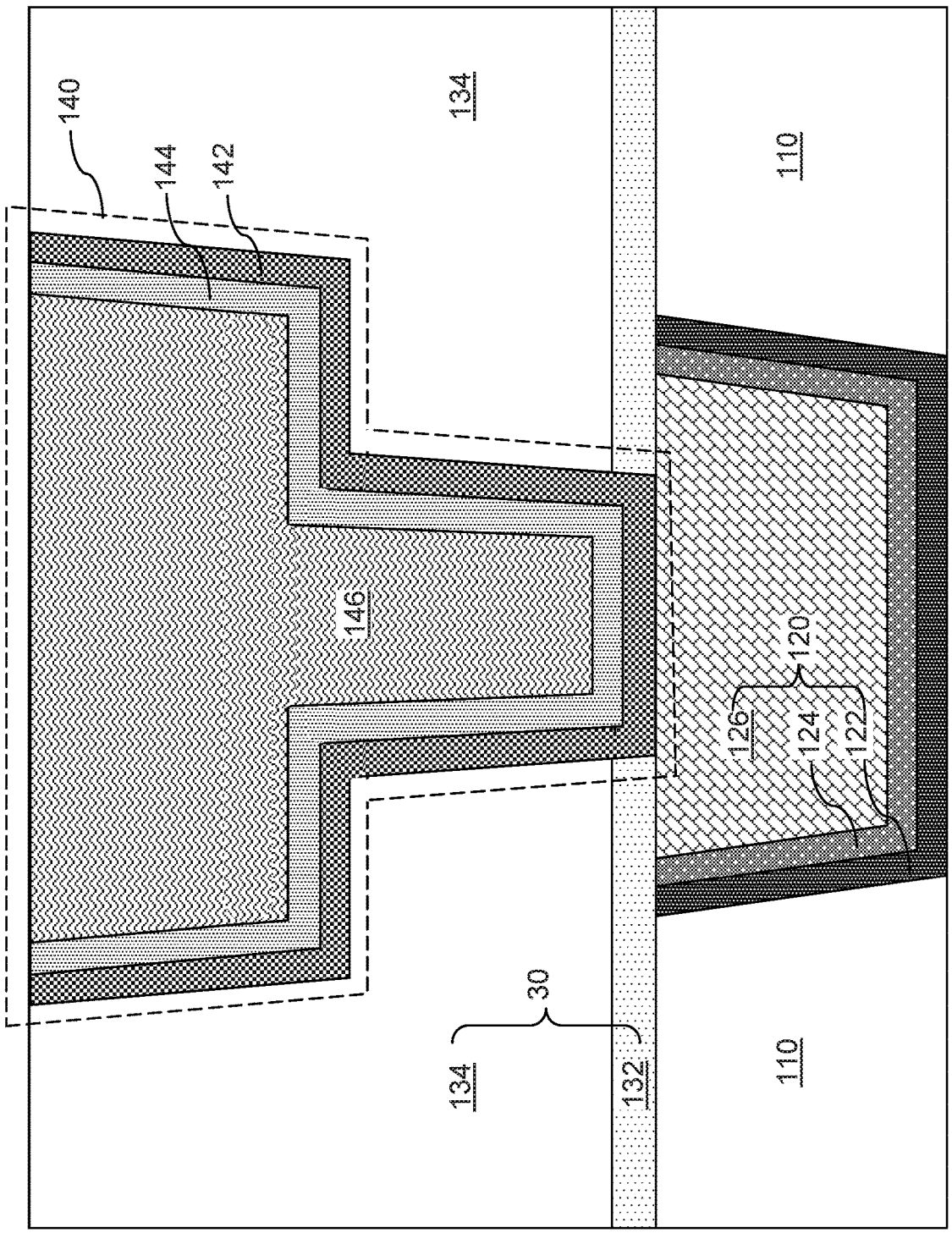
FIG. 15A is a vertical cross-sectional view of a portion of a fifth alternative embodiment of the exemplary structure after formation of a metal interconnect structure according to an embodiment of the present disclosure.

Referring to FIG. 15A, a fifth alternative embodiment of the exemplary structure may be derived from the first alternative embodiment of the exemplary structure of FIG. 11A by forming the opening 131 as a line cavity. In this embodiment, the metal interconnect structure 140 may be formed as an integrated line and structure including a metal line and at least one metal via structure, and the underlying conductive material portion 120 may be a metal line structure or an integrated line and via structure.

Figure 15B:
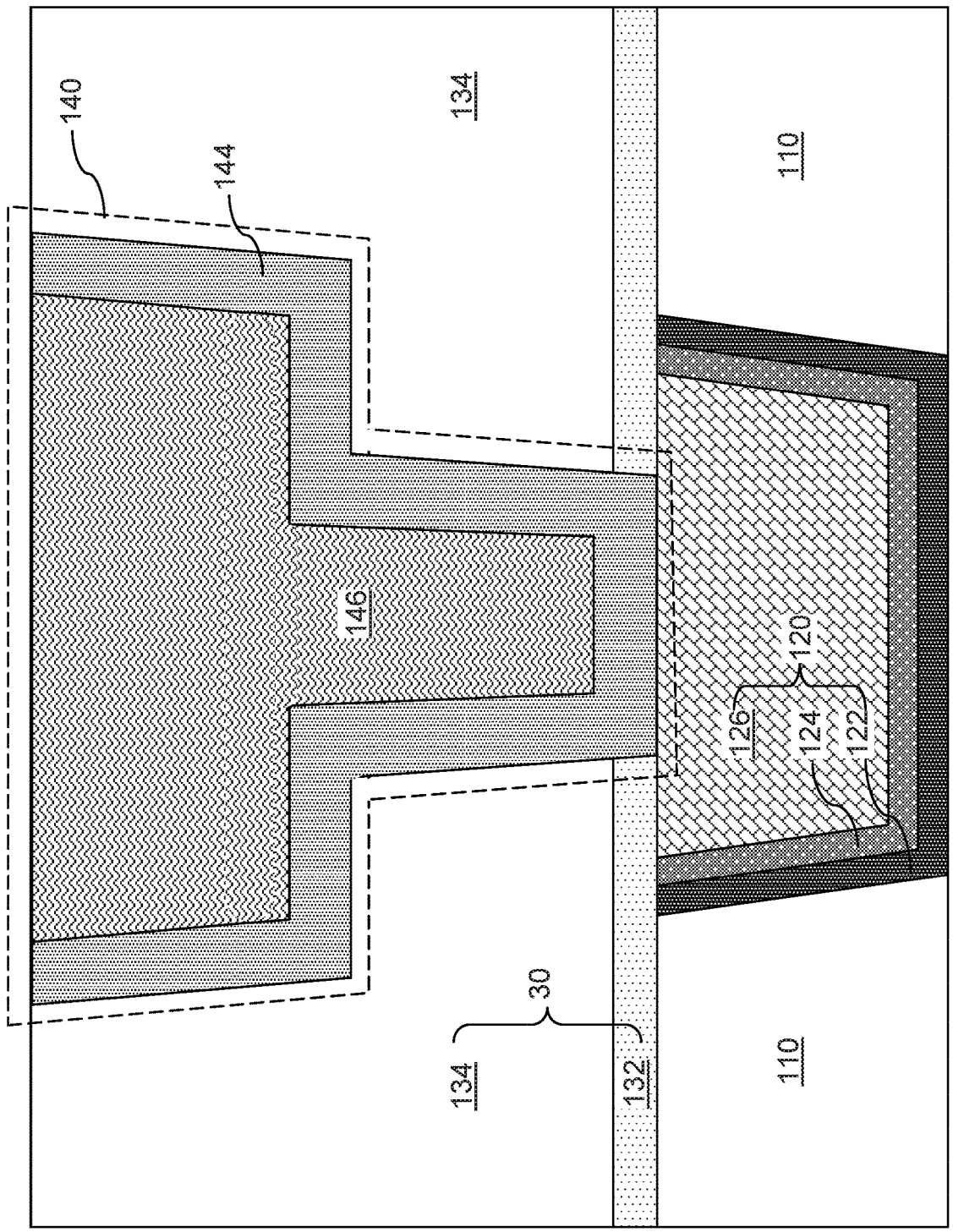
FIG. 15B is a vertical cross-sectional view of another configuration of the exemplary structure of FIG. 15A derived by omission of the metallic nitride liner according to an embodiment of the present disclosure.

FIG. 15B illustrates another configuration of the exemplary structure of FIG. 15A, which can be derived from the exemplary structure of FIG. 15A by omission of the metallic nitride liner 142 according to an embodiment of the present disclosure.

In embodiments in which the underlying conductive material portion 120 includes a metal interconnect structure, the metallic nitride liner 122 may be formed in the same manner as the metallic nitride liner 142 of the embodiments of the present disclosure, the metallic adhesion layer 124 may be formed in the same manner as the metallic adhesion layer 144 of the embodiments of the present disclosure, and the metal fill material portion 126 may be formed in the same manner as the combination of a first metal fill material portion 146 and a second metal fill material portion 148 illustrated in FIGS. 9A, 9B, 12A, 12B, 14A, and 14B, or may be formed in the same manner as a first metal fill material portion 146 illustrated in FIGS. 11A, 11B, 13A, 13B, 15A, and 15B.

Generally, any metal via structure, any metal line structure, and/or any integrated line and via structure illustrated in FIG. 1 may have a configuration of the metal interconnect structure 140 of the present disclosure. Thus, multiple levels of metal interconnect structures 140 may be implemented within the exemplary structure illustrated in FIG. 1.

FIGS. 16A-16D are diagrams illustrating material composition within the first, second, third, and fourth configurations of the metal interconnect structure of the exemplary structure of FIGS. 5A, 5B, 5C, and 5D, respectively. The metallic nitride liner 142 may have a thickness t_mln, which may be in a range from 0.5 nm to 5 nm. The metallic nitride liner 142 includes a conductive metal nitride such as TaN, TiN, and/or WN. The conductive metal nitride may, or may not, be stoichiometric. In embodiments in which the conductive metal nitride is stoichiometric, the ratio of Ta to N, the ratio of Ti to N, or the ratio of W to N may be 1:1.

The metallic adhesion layer 144 has a thickness t_mal, which may be in a range from 0.5 nm to 10 nm. The average atomic percentage of the at least one transition metal element may be in a range from 10% to 90%, such as from 20% to 80%. In one embodiment, the average atomic percentage of the at least one transition metal element may be in a range from 30% to 70%, such as from 40% to 60%. The metallic adhesion layer 144 may consist essentially of the at least one transition metal element and copper. The interface between the metallic adhesion layer 144 and the first copper fill material portion 146 may be defined as a plane at which the atomic percentage of copper is 90% and beyond which the atomic percentage of copper strictly decreases (as the measurement point moves into the first copper fill material portion 146).

Figure 16A:
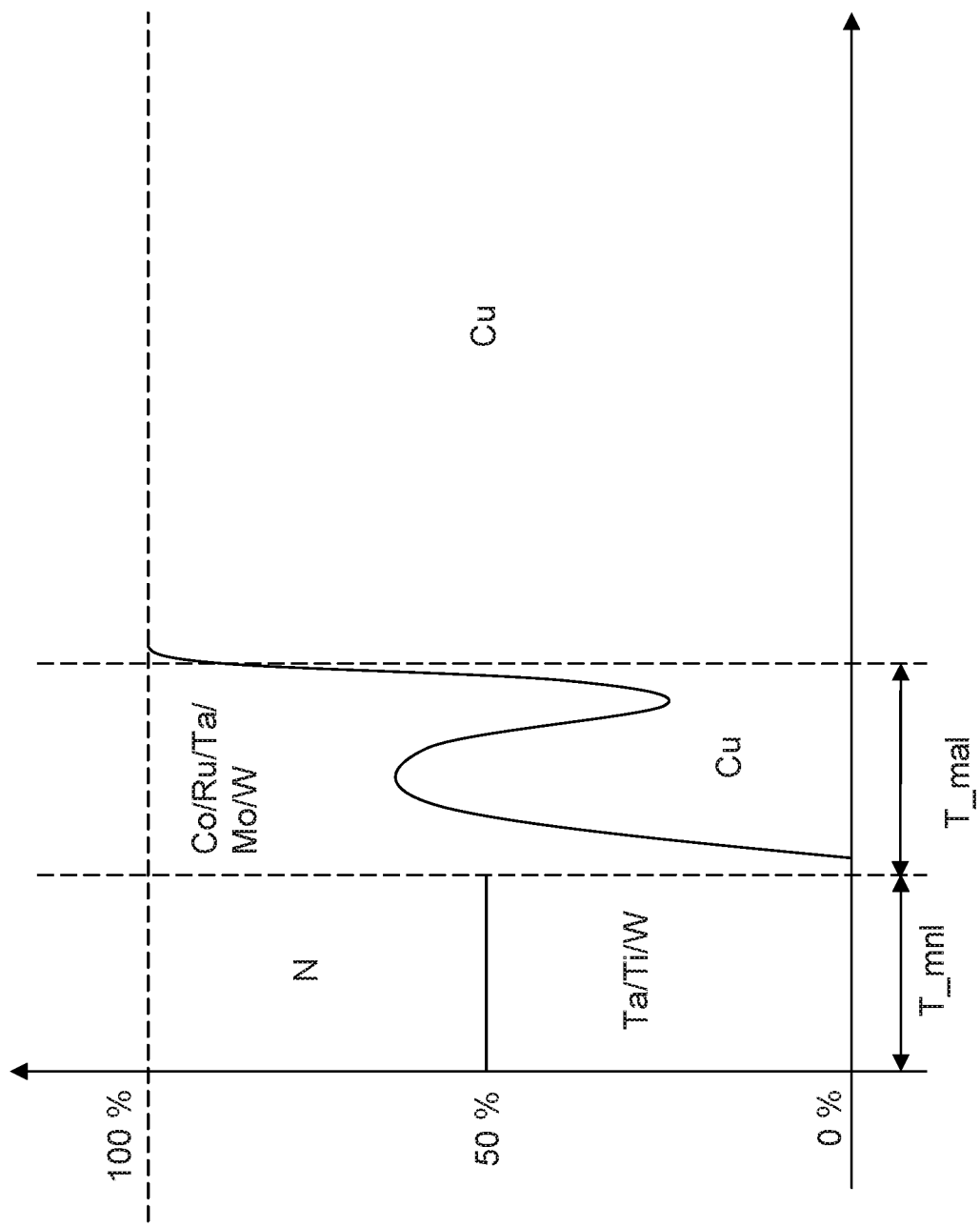

In some embodiments, the material composition in the metallic adhesion layer 144 may have a modulation as a function of a distance from an outer sidewall of the metallic adhesion layer 144 (an interface between the metallic adhesion layer 144 and the metallic nitride liner 142) as illustrated in FIGS. 16A, 16B, 16C. The distance from an outer sidewall of the metallic adhesion layer 144 (such as an interface between the metallic adhesion layer 144 and the metallic nitride liner 142) may be measured, for example, on a sidewall of an opening 131 that vertically extends through the dielectric material layer 134.

In some embodiments, the metallic adhesion layer 144 may have a compositional modulation as a function of a distance from the metallic nitride liner 142, for example, as a function of a distance from an inner sidewall of the metallic nitride liner 142. In some embodiments, the position of a local peak atomic concentration of the at least one transition metal within the metallic adhesion layer 144 may be spaced from an outer sidewall of the metallic adhesion layer 144 (such as an interface between the metallic nitride liner 142 and the metallic adhesion layer 144) as illustrated in FIGS. 16A and 16B. For example, the distance between the position of the local peak atomic concentration of the at least one transition metal and an outer sidewall of the metallic adhesion layer 144 (such as an interface between the metallic nitride liner 142 and the metallic adhesion layer 144) may be in a range from 10% to 100% of a thickness of the metallic adhesion layer 144 (such as the thickness of a vertical or tapered portion of the metallic adhesion layer 144 that contacts a sidewall of the interconnect-level dielectric layer 30) as illustrated in FIGS. 16A and 16B.

In some embodiments, the atomic concentration of copper within the metallic adhesion layer 144 may have a minimum at a location that is spaced from an outer sidewall of the metallic adhesion layer 144 (such as an interface between the metallic nitride liner 142 and the metallic adhesion layer 144) as illustrated in FIGS. 16A and 16B. In some embodiments, the distance between the location of the minimum of the atomic concentration of copper within the metallic adhesion layer 144 and an outer sidewall of the metallic adhesion layer 144 (such as an interface between the metallic nitride liner 142 and the metallic adhesion layer 144) may be in a range from 10% to 100% of the thickness of the metallic adhesion layer 144 (such as the thickness of the metallic adhesion layer 144 over a sidewall of the interconnect-level dielectric layer 30) as illustrated in FIGS. 16A and 16B.

A local peak atomic concentration of copper may occur within the metallic adhesion layer 144 at a distance from an outer sidewall of the metallic adhesion layer 144 (such as an interface between the metallic nitride liner 142 and the metallic adhesion layer 144) as illustrated in FIG. 16A. Alternatively, the atomic concentration of copper within the metallic adhesion layer 144 may have a local maximum at an outer sidewall of the metallic adhesion layer 144 (such as an interface between the metallic nitride liner 142 and the metallic adhesion layer 144) as illustrated in FIG. 16B.

In some embodiments, the position of a local peak atomic concentration of the at least one transition metal within the metallic adhesion layer 144 may be at an outer sidewall of the metallic adhesion layer 144 (such as an interface between the metallic nitride liner 142 and the metallic adhesion layer 144) as illustrated in FIG. 16C. In some embodiments, the atomic concentration of copper within the metallic adhesion layer 144 may have a local minimum at an outer sidewall of the metallic adhesion layer 144 (such as an interface between the metallic nitride liner 142 and the metallic adhesion layer 144) as illustrated in FIG. 16C. In some embodiments, the atomic concentration of copper within the metallic adhesion layer 144 may strictly increase with a distance from an outer sidewall of the metallic adhesion layer 144 (such as an interface between the metallic nitride liner 142 and the metallic adhesion layer 144) as illustrated in FIG. 16C.

Figure 16D:
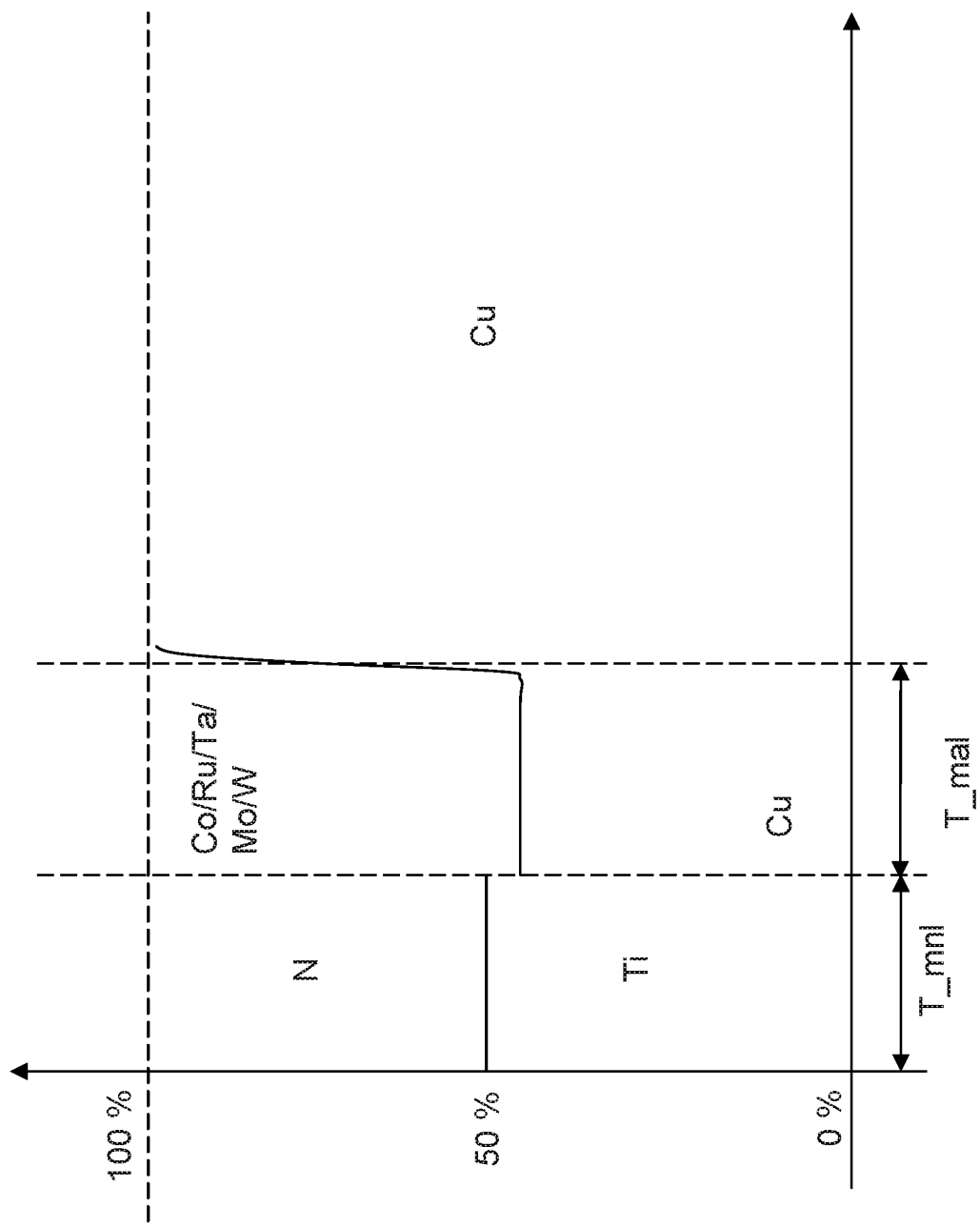

In alternative embodiments, the metallic adhesion layer 144 may be completely homogenized so that the material composition of the metallic adhesion layer 144 is the same throughout the entirety thereof, or throughout at least 80%, and/or at least 90%, of the entire thickness of the metallic adhesion layer 144 as illustrated in FIG. 16D.

Figure 17:
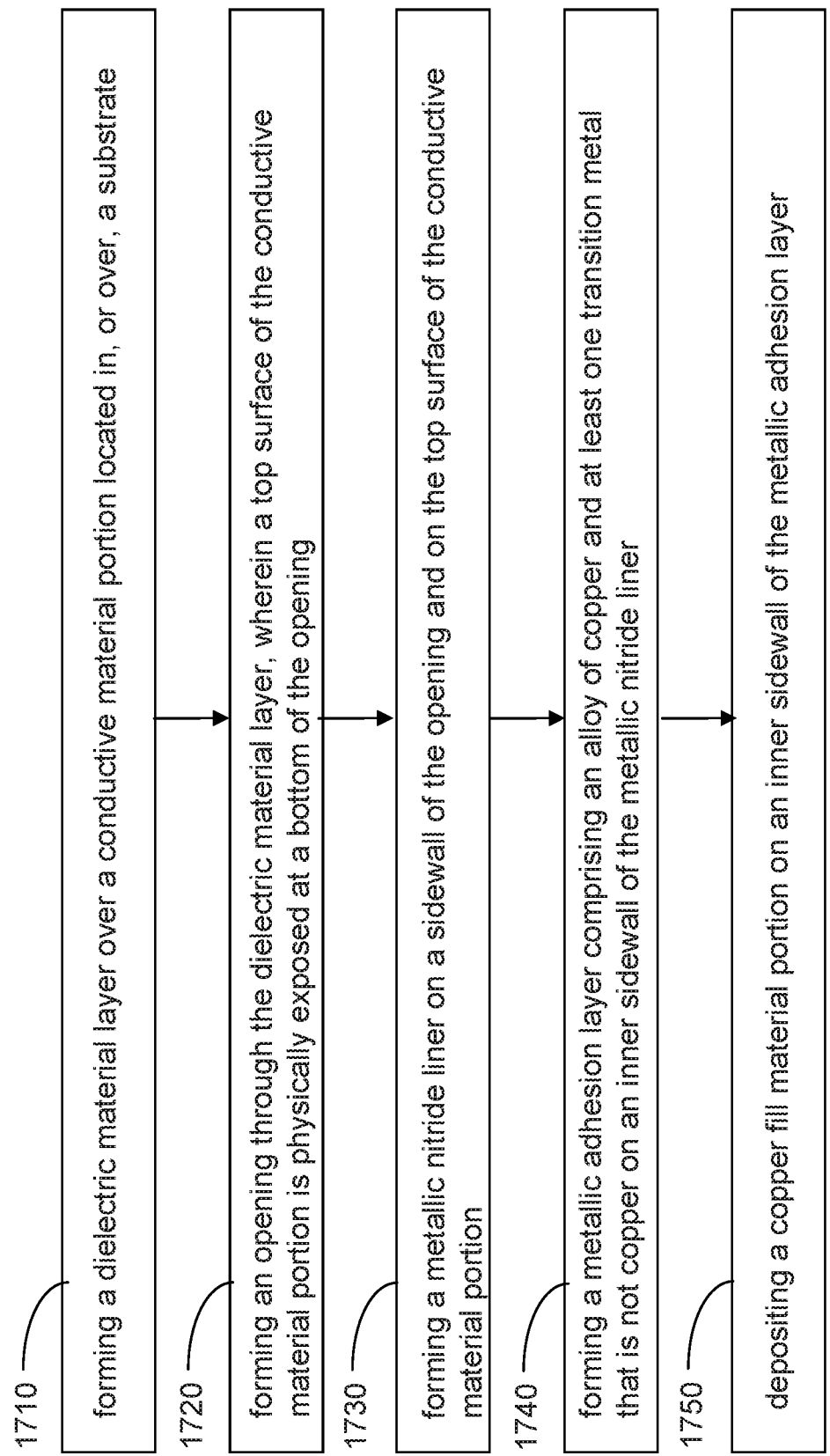
FIG. 17 is a first flowchart that illustrates the general processing steps of methods of the present disclosure.

Referring to FIG. 17, a first flowchart illustrates a set of general processing steps of a method of the present disclosure. Referring to step 1710, a dielectric material layer 30 is formed over a conductive material portion 120 located in, or over, a substrate 8. Referring to step 1720, an opening 131 is formed through the dielectric material layer 30. A top surface of the conductive material portion 120 is physically exposed at a bottom of the opening 131. Referring to step 1730, a metallic nitride liner 142 is formed on a sidewall of the opening 131 and on the top surface of the conductive material portion 120. Referring to step 1740, a metallic adhesion layer 144 comprising an alloy of copper and at least one transition metal that is not copper is formed on an inner sidewall of the metallic nitride liner 142. Referring to step 1750, a copper fill material portion 146 is formed on an inner sidewall of the metallic adhesion layer 144.

Figure 18:
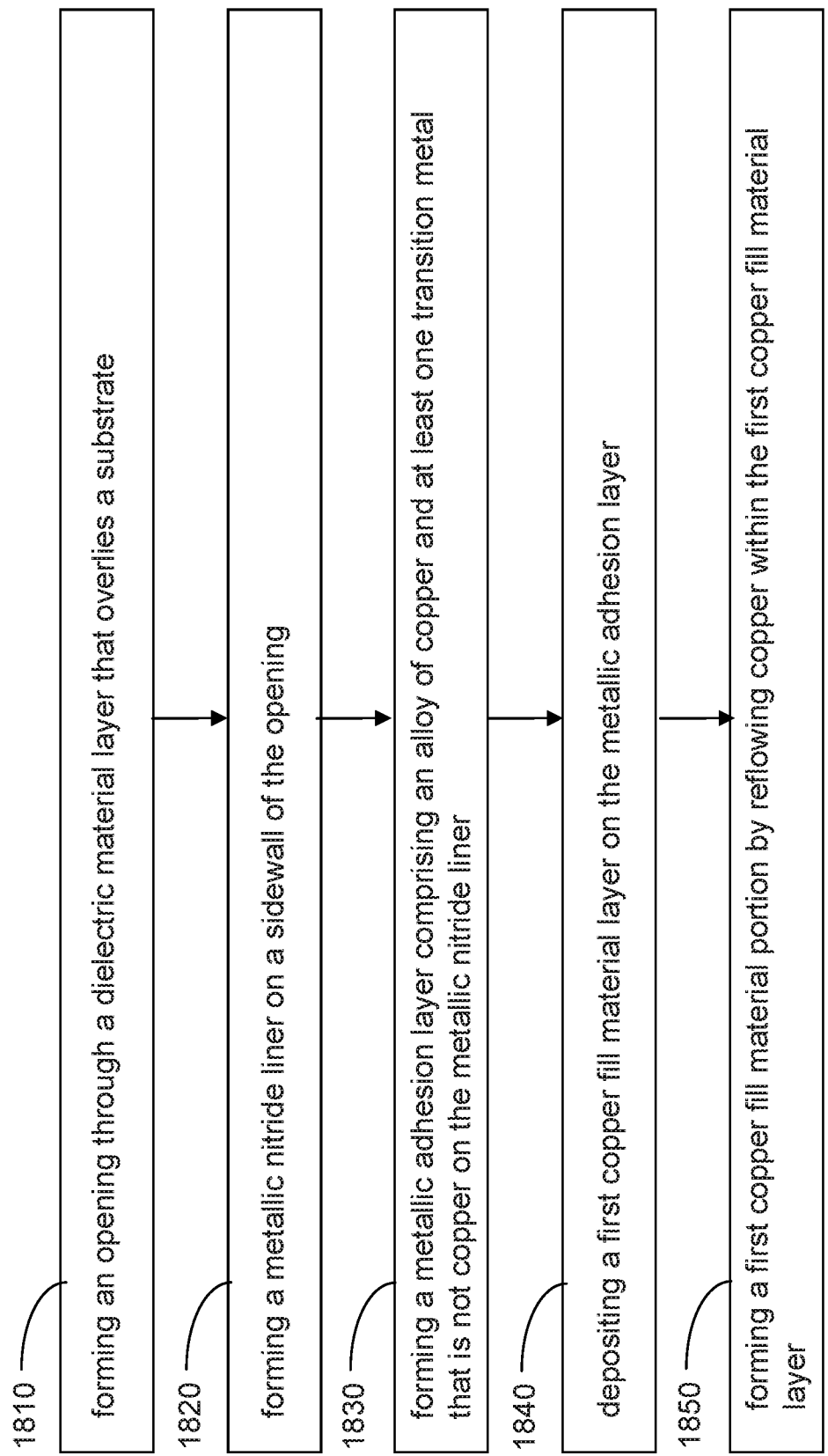
FIG. 18 is a second flowchart that illustrates the general processing steps of methods of the present disclosure.

Referring to FIG. 18, a second flowchart illustrates a set of general processing steps of a method of the present disclosure. Referring to step 1810, an opening 131 is formed through a dielectric material layer 30 that overlies a substrate 8. Referring to step 1820, a metallic nitride liner 142 may be optionally formed on a sidewall of the opening 131. Referring to step 1830, a metallic adhesion layer 144 is formed on the metallic nitride liner 142, or on a sidewall of the dielectric material layer 30 if a metallic nitride liner 142 is not employed. The metallic adhesion layer 144 comprises, and/or consists essentially of, an alloy of copper and at least one transition metal that is not copper. Referring to step 1840, a first copper fill material layer 146L is formed on the metallic adhesion layer 144. Referring to step 1850, copper within the first copper fill material layer 146L is reflowed. A topmost surface of a reflowed portion (such as a first copper fill material portion 146) of the first copper fill material layer 146L is formed underneath a horizontal plane including a top surface of the dielectric material layer 30.

Referring to all drawings and according to various embodiments of the present disclosure, a structure comprising a first metal interconnect structure 140 embedded in a first dielectric material layer 134 and overlying a substrate 8 is provided. The first metal interconnect structure 140 comprises: a metallic adhesion layer 144 comprising an alloy of copper and at least one transition metal that is not copper and located on a sidewall of the first dielectric material layer 134; and a first copper fill material portion 146 located on an inner sidewall of the metallic adhesion layer 144, wherein a position of a local peak atomic concentration of the at least one transition metal within the metallic adhesion layer 144 is spaced from an outer sidewall of the metallic adhesion layer 144 (such as an interface between the metallic nitride liner 142 and the metallic adhesion layer 144).

In one embodiment, a metallic nitride liner 142 can be embedded within, and can be in contact with a sidewall of, the first dielectric material layer 134. In one embodiment, a distance between the position of the local peak atomic concentration of the at least one transition metal and an outer sidewall of the metallic adhesion layer 144 (such as an interface between the metallic nitride liner 142 and the metallic adhesion layer 144) is in a range from 10% to 100% of a thickness of the metallic adhesion layer 144 (such as the thickness of a tapered portion of the metallic adhesion layer 144 that vertically extends through the first dielectric material layer 134).

In one embodiment, an atomic concentration of copper within the metallic adhesion layer 144 has a minimum at a location that is spaced from an outer sidewall of the metallic adhesion layer 144 (such as an interface between the metallic nitride liner 142 and the metallic adhesion layer 144).

In one embodiment, a distance between the location of the minimum of the atomic concentration of copper within the metallic adhesion layer 144 and an outer sidewall of the metallic adhesion layer 144 (such as an interface between the metallic nitride liner 142 and the metallic adhesion layer 144) is in a range from 10% to 100% of a thickness of the metallic adhesion layer 144 (such as the thickness of a tapered portion of the metallic adhesion layer 144 that vertically extends through the first dielectric material layer 134).

In one embodiment, a second metal interconnect structure 120 may be provided, which may include a second copper fill material portion (which may comprise a metal fill material portion 126) and underlying the first dielectric material layer 134. The metallic nitride liner 142 contacts a portion of a top surface of the second copper fill material portion, and the metallic adhesion layer 144 is spaced from the second copper fill material portion and the first dielectric material layer 134 by the metallic nitride liner 142.

In one embodiment, the metallic nitride liner 142 has a thickness in a range from 0.5 nm to 5 nm; and the metallic adhesion layer 144 has a thickness in a range from 0.5 nm to 10 nm. In one embodiment, the at least one transition metal comprises at least one elemental metal selected from Co, Ru, Ta, Mo, and W; and the first copper fill material portion 146 consists essentially of copper. In one embodiment, the first dielectric material layer 134 comprises, and/or consists essentially of, a dielectric material having a dielectric constant in a range from 1.4 to 2.7 (such as a porous organosilicate glass).

In one embodiment, a semiconductor device is located on the substrate 8; and the first metal interconnect structure 140 is electrically connected to a node of the semiconductor device, and comprises a metal via structure, a metal line structure, or an integrated line and via structure.

Referring to all drawings and according to various embodiments of the present disclosure, a method of forming a structure includes forming a dielectric material layer 30 over a conductive material portion 120 located in, or over, a substrate 110. The method further includes forming an opening 131 through the dielectric material layer 30, wherein a top surface of the conductive material portion 120 is physically exposed at a bottom of the opening 131. A metallic nitride liner 142 may be optionally formed on a sidewall of the opening 131 and on the top surface of the conductive material portion 120. The method further includes forming a metallic adhesion layer 144 comprising an alloy of copper and at least one transition metal that is not copper on an inner sidewall of the metallic nitride liner 142, or on a sidewall of the opening 131. The method further includes forming a copper fill material portion 146 on an inner sidewall of the metallic adhesion layer 144.

Referring to all drawings and according to various embodiments of the present disclosure, a method of forming a structure includes forming an opening 131 through a dielectric material layer 30 that overlies a substrate 8. A metallic nitride liner 142 may be optionally formed on a sidewall of the opening 131. The method further includes forming a metallic adhesion layer 144 comprising an alloy of copper and at least one transition metal that is not copper on the metallic nitride liner 142, or on a sidewall of the opening 131. The method further includes depositing a first copper fill material layer 146L on the metallic adhesion layer 144. The method further includes forming a first copper fill material portion 146 by reflowing copper within the first copper fill material layer 146L.

The various embodiments of the present disclosure may be used to provide copper-containing metal interconnect structures without voids. The various embodiments of the present disclosure are particularly effective in forming void-free narrow-pitch metal interconnect structures in which the width of the copper-containing metal interconnect structure is small and/or the aspect ratio of the copper-containing metal interconnect structure is high. The presence of the at least one transition metal element other than copper in the alloy composition of the metallic adhesion layer 144 provides enhanced adhesion to the metallic nitride liner 142. The presence of copper in the alloy composition suppresses dewetting of the surfaces of the metallic nitride liner 142 by the metallic adhesion layer 144, and avoids formation of holes in the metallic adhesion layer 144 during a reflow anneal process. Thus, copper-containing metal interconnect structures may be formed without voids. A metal interconnect assembly including such copper-containing metal interconnect structures may increase the process yield during formation of metal interconnect structures, and may provide semiconductor dies with enhanced reliability.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method of forming a structure, comprising:
    forming an opening through a dielectric material layer that overlies a substrate;
    forming a metallic adhesion layer comprising an alloy of copper and at least one transition metal that is not copper over a sidewall of the opening; and
    forming a copper fill material portion on an inner sidewall of the metallic adhesion layer,
    wherein an atomic concentration of copper within the metallic adhesion layer has a minimum at a location that is spaced from an outer sidewall of the metallic adhesion layer and is spaced from an interface with the copper fill material portion.

2. The method of claim 1, further comprising forming a metallic nitride liner on the sidewall of the opening, wherein the metallic adhesion layer is formed on an inner sidewall of the metallic nitride liner.

3. The method of claim 2, wherein a combination of the copper fill material portion, the metallic adhesion layer, and the metallic nitride liner comprises a metal via structure, a metal line structure, or an integrated line and via structure.

4. The method of claim 1, wherein forming the metallic adhesion layer comprises:
    depositing at least one transition metal layer that consists essentially of the at least one transition metal; and
    depositing at least one copper layer that consists essentially of copper.

5. The method of claim 4, wherein one of the at least one copper layer is deposited prior to deposition of one of the at least one transition metal layer.

6. The method of claim 4, wherein:
    the at least one transition metal layer comprises at least two transition metal layers; and
    one of the at least one copper layer is deposited after deposition of one of the at least two transition metal layers and prior to deposition of another of the at least two transition metal layers.

7. The method of claim 4, further comprising enhancing compositional uniformity of a layer stack including the at least one transition metal layer and the at least one copper layer by performing a plasma treatment process on the layer stack prior to depositing the copper fill material portion.

8. The method of claim 4, further comprising enhancing compositional uniformity of a layer stack including the at least one transition metal layer and the at least one copper layer by performing a thermal anneal process prior to depositing the copper fill material portion.

9. The method of claim 4, wherein one of the at least one copper layer is deposited after deposition of one of the at least one transition metal layer.

10. The method of claim 1, wherein the metallic adhesion layer is formed by a multi-metal deposition process in which copper atoms and atoms of the at least one transition metal are simultaneously deposited to form the alloy of copper and the at least one transition metal.

11. The method of claim 1, wherein:
    the at least one transition metal comprises at least one elemental metal selected from Co, Ru, Ta, Mo, and W; and
    the copper fill material portion consists essentially of copper.

12. The method of claim 1, wherein the metallic adhesion layer comprises a layer stack including at least one copper layer that consists essentially of copper and at least one transition metal layer consisting essentially of the at least one transition metal.

13. The method of claim 1, further comprising:
    forming an etch stop dielectric layer directly on a top surface of the conductive material portion, wherein the dielectric material layer is formed over the etch stop dielectric layer; and
    extending the opening in the dielectric layer through the etch stop dielectric layer.

14. A method of forming a structure, comprising:
    forming an opening through a dielectric material layer that overlies a substrate;
    forming a metallic adhesion layer comprising an alloy of copper and at least one transition metal that is not copper over a sidewall of the opening; and depositing a first copper fill material layer on the metallic adhesion layer, wherein a local peak atomic concentration of copper is present within the metallic adhesion layer at a location that is spaced from an outer sidewall of the metallic adhesion layer and is spaced from an interface with the first copper fill material portion.

15. The method of claim 14, further comprising:
forming a first copper fill material portion by reflowing copper within the first copper fill material layer; and
forming a second copper fill material portion directly on the first copper fill material portion and the metallic adhesion layer.

16. The method of claim 14, further comprising forming a metallic nitride liner on the sidewall of the opening, wherein:
the metallic adhesion layer is formed on the metallic nitride liner, and has a uniform material composition throughout; or
the metallic adhesion layer has a compositional modulation as a function of a distance from the metallic nitride liner.

17. The method of claim 14, wherein the metallic adhesion layer is formed by sequentially depositing:
a first transition metal layer that is deposited directly on the inner sidewall of the metallic nitride liner;
a copper layer that is deposited on the first transition metal layer; and
a second transition metal layer that is deposited on the copper layer.

18. A method of forming a structure, comprising:
forming an opening through a dielectric material layer that overlies a substrate;
forming a metallic nitride layer on the sidewall of the opening;
forming a metallic adhesion layer comprising an alloy of copper and at least one transition metal that is not copper on the metallic nitride layer; and
forming a copper fill material portion on an inner sidewall of the metallic adhesion layer, wherein:
a local peak of an atomic concentration of the at least one transition metal within the metallic adhesion layer is at an outer sidewall of the metallic adhesion layer; and
the atomic concentration of the at least one transition metal within the metallic adhesion layer decreases with a lateral distance from an interface between the metallic adhesion layer and the metallic nitride layer.

19. The method of claim 18, wherein the metallic adhesion layer is formed by a multi-metal deposition process in which copper atoms and atoms of the at least one transition metal are simultaneously deposited to form the alloy of copper and the at least one transition metal.

20. The method of claim 19, wherein:
the at least one transition metal comprises at least one elemental metal selected from Co, Ru, Ta, Mo, and W; and
the copper fill material portion consists essentially of copper.

* * * * *